US011110269B2

(12) United States Patent
Gregson

(10) Patent No.: US 11,110,269 B2
(45) Date of Patent: Sep. 7, 2021

(54) ELECTROSTIMULATION RELATED DEVICES AND METHODS

(71) Applicant: FEMEDA LTD., Cramlington (GB)

(72) Inventor: Ian Gregson, Wigan (GB)

(73) Assignee: FEMEDA LTD., Cramlington (GB)

( * ) Notice: Subject to any disclaimer, the term of this patent is extended or adjusted under 35 U.S.C. 154(b) by 212 days.

(21) Appl. No.: 15/500,896

(22) PCT Filed: Aug. 19, 2015

(86) PCT No.: PCT/EP2015/069095
§ 371 (c)(1),
(2) Date: Jan. 31, 2017

(87) PCT Pub. No.: WO2016/026914
PCT Pub. Date: Feb. 25, 2016

(65) Prior Publication Data
US 2017/0216576 A1 Aug. 3, 2017

(30) Foreign Application Priority Data
Aug. 19, 2014 (GB) ...................................... 1414695

(51) Int. Cl.
*A61N 1/05* (2006.01)
*A61N 1/36* (2006.01)
*A61N 1/372* (2006.01)

(52) U.S. Cl.
CPC ....... *A61N 1/0524* (2013.01); *A61N 1/36007* (2013.01); *A61N 1/36125* (2013.01);
(Continued)

(58) Field of Classification Search
CPC .............. A61N 1/0524; A61N 1/36007; A61N 1/36125; A61N 1/36146; A61N 1/36153; A61N 1/37211
See application file for complete search history.

(56) References Cited

U.S. PATENT DOCUMENTS 3,640,284 A 2/1972 Langis
3,650,275 A 3/1972 Von Der Mozel
(Continued)

FOREIGN PATENT DOCUMENTS

CN 101370552 2/2009
CN 102139139 8/2011
(Continued)

OTHER PUBLICATIONS

International Search Report issued in corresponding International Application No. PCT/EP2006/011288 filed Nov. 24, 2006.
(Continued)

*Primary Examiner* — Catherine M Voorhees
*Assistant Examiner* — Roland Dinga
(74) *Attorney, Agent, or Firm* — Knobbe Martens Olson and Bear, LLP

(57) ABSTRACT

There is disclosed a device and method for delivering constant target current to a muscle for electro-stimulation of that muscle. One device is a completely self-contained device with no external means for the adjustment and control of the electro-stimulation delivered to the muscle during treatment. The microprocessor based device monitors indirectly the actual current delivered to the muscle during electro-stimulation via measurement of the return path voltage through the muscle and optionally in addition monitors and adjusts for the internal battery voltage during use of the device in order to deliver a more consistent an accurate and effective target output current to the muscle being stimulated at each and every pulse delivered from the device. The device is pre-programmed with an electro-stimulation treatment cycle and the whole treatment cycle, including the monitoring and adjustment required to achieve this treatment cycle, is automatic within the device.

35 Claims, 6 Drawing Sheets

(52) U.S. Cl.
CPC ..... *A61N 1/36146* (2013.01); *A61N 1/36153*
(2013.01); *A61N 1/37211* (2013.01)

(56) References Cited

U.S. PATENT DOCUMENTS

| | | |
|---|---|---|
| 3,800,800 A | 4/1974 | Garbe et al. |
| 3,933,147 A | 1/1976 | Du Vall |
| 3,943,938 A | 3/1976 | Wexler |
| 3,973,571 A | 8/1976 | Suhel |
| 4,106,511 A | 8/1978 | Erlandsson |
| 4,515,167 A | 5/1985 | Hochman |
| 4,580,578 A | 4/1986 | Barson |
| 4,688,575 A | 8/1987 | Duvall |
| 4,785,828 A | 11/1988 | Maurer et al. |
| 4,873,996 A | 10/1989 | Maurer |
| 4,881,526 A | 11/1989 | Johnson et al. |
| 4,909,263 A | 3/1990 | Norris |
| 4,911,149 A | 3/1990 | Borodulin |
| 5,045,079 A | 9/1991 | West |
| 5,046,511 A | 9/1991 | Maurer |
| 5,063,929 A | 11/1991 | Bartelt et al. |
| 5,117,840 A | 6/1992 | Brenman et al. |
| 5,199,443 A | 6/1993 | Maurer et al. |
| 5,314,465 A | 5/1994 | Maurer et al. |
| 5,370,671 A | 12/1994 | Maurer et al. |
| 5,376,206 A | 12/1994 | Maurer et al. |
| 5,385,577 A | 1/1995 | Maurer et al. |
| 5,456,709 A | 10/1995 | Hamedi |
| 5,516,396 A | 5/1996 | Maurer et al. |
| 5,571,118 A | 5/1996 | Boutos |
| 5,562,717 A | 10/1996 | Tippey et al. |
| 5,662,699 A | 2/1997 | Hamedi |
| 5,618,256 A | 4/1997 | Reimer |
| 5,667,615 A | 9/1997 | Maurer et al. |
| 5,702,428 A | 12/1997 | Tippey et al. |
| 5,759,471 A | 2/1998 | Maurer et al. |
| 5,800,501 A | 9/1998 | Sherlock |
| 5,800,502 A | 9/1998 | Boutos |
| 5,816,248 A | 10/1998 | Anderson et al. |
| 5,871,533 A | 2/1999 | Boutos |
| 5,875,778 A | 3/1999 | Vroegop |
| 5,881,731 A | 3/1999 | Remes |
| 5,921,944 A | 7/1999 | Borodulin |
| 6,063,045 A | 5/2000 | Wax |
| 6,086,549 A | 11/2000 | Neese et al. |
| 6,185,465 B1 | 2/2001 | Mo et al. |
| 6,240,315 B1 | 5/2001 | Mo |
| 6,264,582 B1 | 7/2001 | Remes |
| 6,289,245 B1 | 9/2001 | Mo |
| 6,321,116 B1 | 11/2001 | Mo |
| 6,432,037 B1 | 8/2002 | Eini et al. |
| 6,449,512 B1 | 9/2002 | Boveja |
| 6,470,219 B1 | 10/2002 | Edwards et al. |
| 6,631,297 B1 | 7/2003 | Mo |
| 6,865,423 B2 | 3/2005 | Oldham |
| 8,509,900 B2 | 8/2013 | Boyd et al. |
| 8,805,509 B2 | 8/2014 | Boyd et al. |
| 9,042,987 B2 | 5/2015 | Boyd et al. |
| 9,358,383 B2 | 6/2016 | Boyd et al. |
| 9,381,345 B2 | 7/2016 | Boyd et al. |
| 9,526,903 B2 | 12/2016 | Boyd et al. |
| 10,105,531 B2 | 10/2018 | White |
| 2002/0000233 A1 | 1/2002 | Jude |
| 2002/0068900 A1 | 6/2002 | Barnes |
| 2003/0004553 A1 | 2/2003 | Grill |
| 2003/0083590 A1 | 5/2003 | Hochman et al. |
| 2003/0135245 A1 | 7/2003 | Campos |
| 2003/0087734 A1 | 8/2003 | Kring |
| 2003/0220589 A1 | 11/2003 | Leisveth et al. |
| 2004/0030360 A1 | 2/2004 | Eini et al. |
| 2004/0054392 A1 | 3/2004 | Dijkman |
| 2004/0122341 A1 | 4/2004 | Walsh |
| 2004/0236385 A1 | 11/2004 | Rowe |
| 2005/0228316 A1 | 10/2005 | Morgenstern |
| 2006/0247739 A1 | 11/2006 | Wahlstrand et al. |
| 2006/0265027 A1 | 11/2006 | Vaingast et al. |
| 2007/0112327 A1* | 5/2007 | Yun ............... A61K 9/0034 604/500 |
| 2009/0228067 A1* | 9/2009 | Boyd ............... A61N 1/0512 607/48 |
| 2011/0264171 A1* | 10/2011 | Torgerson ............ A61N 1/36 607/59 |
| 2012/0101326 A1* | 4/2012 | Simon ............ A61N 1/36034 600/9 |

FOREIGN PATENT DOCUMENTS

| | | |
|---|---|---|
| DE | 3518317 | 11/1986 |
| DE | 3827232 | 11/1989 |
| DE | 3919453 | 12/1989 |
| DE | 4035267 | 5/1991 |
| DE | 4022074 | 2/1992 |
| DE | 4436634 | 4/1996 |
| DE | 19715870 | 10/1998 |
| DE | 19755243 | 6/1999 |
| DE | 10162484 | 7/2003 |
| EP | 0088173 | 9/1983 |
| EP | 178514 | 4/1986 |
| EP | 0263466 | 4/1988 |
| EP | 0411632 | 2/1991 |
| EP | 473131 | 3/1992 |
| EP | 638329 | 2/1995 |
| EP | 1279413 | 1/2003 |
| EP | 1704892 | 9/2006 |
| FR | 2547203 | 12/1984 |
| FR | 2655271 | 6/1991 |
| FR | 2709252 | 3/1995 |
| FR | 2709422 | 3/1995 |
| FR | 2762983 | 5/1997 |
| FR | 2754717 | 4/1998 |
| FR | 2757070 | 6/1998 |
| FR | 2767481 | 2/1999 |
| FR | 2806634 | 9/2001 |
| FR | 2827520 | 1/2003 |
| GB | 1480103 | 7/1977 |
| GB | 1599466 | 10/1981 |
| GB | 2 404 339 | 2/2005 |
| JP | 57-037456 | 8/1980 |
| JP | 61-103149 U | 7/1986 |
| JP | 63-281663 | 4/1987 |
| JP | 9122248 | 5/1997 |
| JP | 11019223 | 1/1999 |
| JP | 2006167385 | 6/2006 |
| JP | 2013-48510 | 3/2013 |
| JP | 2013-126590 | 6/2013 |
| NL | 8902023 | 8/1989 |
| WO | WO1984001515 | 4/1984 |
| WO | WO 84/03211 | 8/1984 |
| WO | WO1992014510 | 9/1992 |
| WO | WO1993024176 | 12/1993 |
| WO | WO1997031679 | 9/1997 |
| WO | WO 97/47357 | 12/1997 |
| WO | WO1997048446 | 12/1997 |
| WO | WO 98/34677 | 8/1998 |
| WO | WO9935986 | 7/1999 |
| WO | WO2000006246 | 2/2000 |
| WO | WO2000062699 | 10/2000 |
| WO | WO 01/60446 | 8/2001 |
| WO | WO 01/95829 | 12/2001 |
| WO | WO2002009805 | 2/2002 |
| WO | WO 03/007862 | 1/2003 |
| WO | WO2005077276 | 8/2005 |
| WO | WO 2007/145913 | 12/2007 |
| WO | WO 2007/145913 A1 | 12/2007 |
| WO | WO 2016/026914 | 2/2016 |

OTHER PUBLICATIONS

International Search Report issued in corresponding PCT International Application No. PCT/EP2006/011286 dated Mar. 8, 2007.
Ohlsson, et al., "Miniaturised Device for Long-Term Intravaginal Electrical Stimulation for the Treatment of Urinary Incontinence,"

(56) References Cited

OTHER PUBLICATIONS

Medical and Biological Engineering and Computing, vol. 26, No. 5, Sep. 1, 1988, pp. 509-515.

International Search Report issued in corresponding International Application No. PCT/EP2006/011287 filed Nov. 24, 2006.

Jeyaseelan, S.M. et al., "An evaluation of a new pattern of electrical stimulation as a treatment for urinary stress incontinence: a randomized, double-blind, controlled trial", Clinical Rehabilitation, 2000, p. 631-640, 14, SAGE Publications.

International Search Report and Written Opinion issued in corresponding International Application No. PCT/EP2016/069095 filed Aug. 11, 2016.

Dong-Mei et al., "Feature collection and analysis of surface electromyography signals", Journal of Clinical Rehabilitative Tissue Engineering Research, Oct. 22, 2010, vol. 14, No. 43. p. 8073-8077.

\* cited by examiner

ELECTROSTIMULATION RELATED DEVICES AND METHODS

CROSS-REFERENCE TO RELATED APPLICATIONS

This application is a U.S. National Phase of PCT International Application No. PCT/EP2015/069095, filed on Aug. 19, 2015, which claims the priority benefit under 35 U.S.C. § 119 of United Kingdom Patent Application No. 1414695.5, filed on Aug. 19, 2014. Each of these applications is hereby incorporated by reference in its entirety.

FIELD OF INVENTION

The present invention is concerned with devices and methods related to the electro-stimulation of muscle. In particular but not exclusively to electro-stimulation devices and methods related to the electro-stimulation of the musculature of the pelvic floor.

BACKGROUND ART

Caring for women with pelvic floor disorders has become an increasingly important component of women's healthcare. These disorders, which include urinary and faecal incontinence, sexual dysfunction as well as pelvic organ prolapse, affect a large segment of the adult female population. One common cause is trauma during vaginal delivery which may result in a variety of pelvic floor complaints; urinary stress and urge incontinence and faecal incontinence are the most frequent and long lasting. Ultimately conditions associated with pelvic floor disorders may have a significant impact on the lives of women and may require corrective surgery, which is costly and undesirable and in some instances not totally effective.

There is an increasing emphasis on seeking to avoid such detrimental outcomes through the use of various approaches to controlling and improving pelvic floor muscle function through regular or programmed periods of pelvic floor muscle exercise.

In one example in order to restore function of the pelvic floor muscles after childbirth, women have been encouraged to perform pelvic floor muscle exercises. Pelvic floor muscle exercises (PFME) are a known treatment for exercising muscles which control urinary function. Pelvic floor muscle exercises are also called Kegel exercises after Dr. Arnold Kegel, who in the late 1940's, promoted them to strengthen the pelvic floor muscles. Such exercises require the relevant muscles to be contracted and relaxed regularly during the course of a day for a period of many weeks, often months. There is a significant issue of adherence to such exercise regimens with many women failing to perform the exercises correctly, or failing to practice them regularly or for sufficient duration to achieve effective outcomes. A known aid for such exercises in women comprises a pre-formed core of rigid plastics material. Such aids are provided in a set of graded weights, requiring the woman to insert them into the vagina, and retain them in position. However, this can be difficult for some women. The smallest available weight may be too heavy, or the size is incorrect. For many women the correct positioning of the device is problematic. These devices are also not suitable for use by women with moderate or severe genito-urinary prolapse.

A variety of non-surgical approaches have been investigated as treatments of urinary incontinence, including various forms of PFME, biofeedback techniques based on measuring the physical performance of the muscles and muscle strength, other behavioral therapies, and through neuromuscular electrical stimulation (NMES) of the pelvic floor muscles.

NMES involves the electrical stimulation of the pelvic floor muscles using a probe or skin electrodes connected to a device for controlling the electrical stimulation. People receiving NMES may undergo treatments in a clinical setting such as a hospital, or may undergo initial training in a clinician's office followed by home treatment with a rented or purchased pelvic floor stimulator that has been programmed to their perceived needs by the clinician. A trained clinician will be able to assess the type of incontinence and the function of the pelvic floor muscles of an individual woman and be able to programme the stimulation unit to deliver an individualized treatment. A significant limitation of conventional stimulation units is that they use rigid vaginal electrodes and in order to retain the electrode during treatment the woman needs to remain still, and dependent upon the electrode often in a recumbent position. The electrode is commonly hard-wired to an external control unit or in some cases it can be wirelessly connected to an external control unit. However, the need to be connected to the control unit in some way also restricts the freedom to move around during treatment. These factors have a negative impact on the adherence of women to using conventional NMES treatment.

Home use or user controllable electro-stimulation devices have similar problems. Such devices typically have controls that allow the user to set and operate the electro-stimulation device. User control and adjustment of the electro-stimulation is conventionally provided by electronic push switches and or rotational control knobs for various parameters for the electro-stimulation. These means of control are typically either located on the surface of the stimulation device or probe and are exposed from the body during use of the device or they are located on a control unit exterior to the user's body and connected, via a cable or wirelessly, to a stimulation probe located within the user's body. The use of such devices with controls is problematic because most non-expert users find it very difficult to control the device and to optimize the settings for effective electro-stimulation of their pelvic floor muscles. Typically these units come with a choice of pre-set programmes relating to the type of incontinence. If used without clinician input there is a risk that the woman does not understand her condition sufficiently well enough to be able to select the correct programme. Due to the nature of NMES applied externally to muscles, typically the sensory nerves respond to the stimulation prior to the motor nerves which produce the contraction. A woman using a home NMES device is therefore at risk of sensing the stimulation at the first sensory level and in assuming that this is the therapeutic level never reaches a motor effect and the true therapeutic level thus resulting in ineffective treatment.

Conventional NMES units, whether used with a clinician or at home by the user, do not have automatic adjustment. Whilst the intensity level, typically voltage, can be manually changed for comfort or to improve the level of contraction typically this would only occur a few times during a treatment (if at all) and typically on an ad hoc basis.

Thus a major challenge with these conventional devices and conventional exercise regimens is to achieve an effective exercise level and/or to achieve a reasonable level of adherence in order to realize the benefits of the exercise, whilst reducing the negative impacts on user's time and lifestyles. In order to address this issue attempts have been made to develop electro-stimulation devices for pelvic floor exercise that are much easier to use, do not require physician or therapist engagement and which do not require any adjustment or control of the electro-stimulation exercise program by the user before or during use.

Examples of such devices are as described in WO2007/059988 and WO2007/059989. In these devices a pre-determined operation voltage and treatment/exercise cycle of pulse frequencies and patterns are programmed into a microchip, which is located within the body of the device and the whole device is inserted into the vagina with closure of the introitus to the vagina.

Whilst such devices are a significant improvement over more conventional prior art devices and regimens there is a need for further improvement to secure effective exercise of the pelvic floor muscles in particular and especially when users are mobile and for a wide range of potential users.

DISCLOSURE OF THE INVENTION

The present invention is in part predicated on a much better understanding of the characteristics of the pelvic floor musculature in women than was hitherto known and which has a major impact on the effectiveness of electro-stimulation of this region. This understanding eluded the prior attempts to provide an effective exercise regimen either through conventional means or through the use of automatic or semi-automatic devices for a number of reasons. This was either because there were presumptions as to the nature and properties of the musculature in this region of the body and/or the operating conditions of prior art devices and exercise regimens were operated in such a manner that these properties were masked and not exposed. Within any treatment regimen there would be a number of separate treatment or electro-stimulation events delivered via use of an electro-stimulation device with an electro-stimulation treatment cycle for each event. Thus within any given treatment regimen there would typically be multiple separate treatment events and each event could use the same or a different electro-stimulation treatment cycle.

It is known in the art of electro-stimulation that all muscles have a degree of resistance or impedance, which means they conduct electricity to varying degrees. In practice what this means is a certain level of power is required to push the electricity into the muscle effectively to achieve electro-stimulation. In relation to the muscle region of the pelvic floor conventional electro-stimulation devices have been conceived and designed on prevailing assumptions and understandings as to the properties and behavior of the muscle region of the pelvic floor. Whilst it is known that pelvic floor muscle impedance changes throughout an individual woman's menstrual cycle, what has now been discovered in the first instance is that the range of impedances of the pelvic floor across a diverse population of women is significantly broader than expected and in the second instance it has also been discovered that for any particular individual the impedance of the pelvic floor region varies significantly over a relatively short period of time that may equate to a single normal electro-stimulation treatment cycle. If for example the individual is not static and relaxed as may be the case during physical exercise or even just standing up from a sitting or prostrate position the impedance will vary significantly and unpredictably. State of the art devices and in particular self-contained devices are unable to address this level of variance and therefore cannot deliver consistent and effective electro-stimulation across this range of variance.

These variances have hitherto not been studied nor effectively accommodated in any electro-stimulation exercise regimen because of the conventional modus operandi for NMES with either physician control or user control. This has in part lead to a belief that at a given treatment event or point in the event, observed sensitivity and lack of treatment tolerance was occurring due to incorrect device settings or application of the device; this being 'corrected by changes in any number of the devices settings and cycle profile at that event. This lack of understanding about the true diversity of impedance properties is one reason why hitherto it has been a major challenge to develop a self-contained and pre-programmed electro-stimulation device that is capable of effectively electro-stimulating a diverse range of women and also able to accommodate the unpredictable and surprising variance in the impedance in a single woman during a single electro-stimulation event.

Thus one objective of the present invention is to provide an electro-stimulation device, which is a self-contained device for complete insertion into the vagina and which operates automatically to accommodate and adjust to wide variances in pelvic floor impedance in order to deliver effective electro-stimulation to this region. That is a device which has feedback means for automatically adjusting to compensate for the differences in muscle impedance between different users and for the changes within individual users and particularly if the woman is mobile during electro-stimulation. Such a device may be effectively used by a much broader range of women and in individual women during a range of normal lifestyle activities, whilst automatically delivering a consistent level of effective exercise to the pelvic region that was hitherto not possible with conventional devices.

In a further objective the feedback means for automatically adjusting to compensate for the differences and changes in muscle impedance may also be used with conventional devices, which are non-self-contained to provide more consistent and effective exercise of the pelvic floor. Modifications to conventional systems may allow the use of the impedance related feedback to ensure optimum exercise of muscles for example under physician or user control. It is believed that although not fully automatic the use of this technique will allow more effective manual settings and/or semi-automatic operation to provide more effective exercise regimes in these environments. In this embodiment the user and/or clinician may be given an indication as to whether or not a target output is actually being delivered to the muscle under electro-stimulation and thus remove the high levels of subjectivity present in conventional treatment regimens.

These objectives are realized through an effective measurement, feedback and control mechanism. Upon commencement of a pulsed electro-stimulation cycle measurements taken during an initial pulse and processing of those measurements enables determination of the effectiveness of the initial pulse in delivering the required electro-stimulation. This determination is then used to adjust the operation parameters for subsequent electro-stimulation to deliver the required electro-stimulation effect. In preferred embodiments of the invention the electro-stimulation is delivered at an initial voltage level selected to deliver a target electro-stimulation output current to the muscle; subsequent measurements and processing determines if the target output current has been delivered to the muscle and if not then appropriate adjustment control is implemented to automatically adjust the voltage level for subsequent electro-stimulation in order to attain the target output current. In the preferred embodiment the current delivered to the muscle is determined through the measurement of a return path voltage through the muscle. Assessment of this return path voltage with automatic adjustment of the voltage level for subsequent electro-stimulation pulses enables more effective and consistent delivery of the target output current to the muscle in order to achieve an effective treatment of the pelvic floor. This feedback mechanism may continue to operate and preferably does continue to operate throughout the treatment cycle and effectively manages the voltage level required to maintain a consistent and appropriate level of target output current even though the muscle impedance is varying throughout the treatment cycle. Thus any device using this mechanism is able to automatically adapt to the muscle tone and environment of any particular individual or changes within an individual to deliver an optimized exercise for the pelvic floor muscle.

Thus in a first aspect the present invention provides an electro stimulation device for delivering a target pulsed output current to muscle in contact with the device, which device comprises:
 a) a device body,
 b) at least two electrodes for delivery of pulsed electro-stimulation current to muscle,
 c) at least one source of power, and
 d) at least one control unit comprising means for generating a required output voltage to achieve a target output current, means for measuring return path voltage through the muscle from an initial decay period of an electro-stimulation pulse and means for adjusting the output voltage required to achieve a target output current for subsequent electro-stimulation based on the measurement of return path voltage.

In a second aspect the present invention provides a method for delivering a target output current to a muscle via pulsed electro-stimulation, which method comprises stimulating the muscle via pulsed electro-stimulation at an initial voltage level selected to deliver the target output current, measuring return path voltage within the circuit including the muscle at the initial voltage level, and based upon the measured return path voltage adjusting the voltage level of subsequent electro-stimulation to deliver the target output current level to the muscle.

In a third aspect the present invention provides a method for measuring the relative impedance within a circuit comprising muscle, which method comprises applying an output voltage to a muscle via at least two electrodes forming a circuit with the muscle, measuring the return path voltage within the circuit through the electro-stimulated muscle and comparing the applied output voltage to the return path voltage to calculate a relative impedance value for the circuit comprising muscle.

In a fourth aspect the present invention provides a device for measuring the relative impedance of a muscle under a pulsed electro-stimulation, which device comprises:
 a) at least two electrodes for delivery of pulsed electro-stimulation current to muscle,
 b) at least one source of power, and
 c) at least one control unit, comprising circuit means for generating and delivering pulsed electro-stimulation current to muscle, means for generating an output voltage to be applied to the muscle via the electrodes, means for measuring the return path voltage through the electro-stimulated muscle from an initial decay period of an electro-stimulation pulse, and processing means for determining the relative impedance of the muscle through a comparison of the applied output voltage to the return path voltage.

With reference to all aspects of the present invention the devices and methods may include means and methods for the collection and/or storage of data generated upon operation of the device or measured during operation of the device and in particular relative impedance, voltage levels, measured current, return path voltage, stimulation pulse profiles, pulse duration, pulse frequency, battery levels and any other parameters measured or calculated and including the time at which all parameters are measured or calculated. This data may be stored within the device for later extraction or may be extracted from the device in real time or at regular intervals in the electro-stimulation cycle during a treatment event. This data may be extracted from used devices through connection to a computer or other data extraction means via a programming adaptor and for example through the device electrodes. Alternatively the device may incorporate means for transmitting the data via wireless or other transmission means to a receiver that is remote from the device during use or after use of the device. This data may be accumulated and analyzed to provide useful information as to the condition of the user's pelvic floor muscles and/or the effectiveness of an individual electro-stimulation event or a whole treatment regimen. Over a period of time and with large groups of users useful information may be gathered for epidemiological studies that may be used to improve device design, the treatment cycles for each treatment event of self-contained or conventional devices and treatment regimens.

The devices and methods of aspects of the present invention may be modified versions of those devices and methods as described in WO2007/059988 and WO2007/059989, the whole contents of which are hereby incorporated by reference. The modification being inclusion of one or more of the aspects of the present invention not already present in the devices and methods in these disclosures.

It is preferred that in all aspects of the present invention that the device is a self-contained device. By self-contained is meant a device in which all of the components of the device are located within a defined device body with at least two electrodes at or on the exterior surface of the device body and wherein the device comprises all control means and relevant circuit components within the device body and the control means are pre-programed for the electro-stimulation treatment cycle with no external means of control or alteration of this pre-programed electro-stimulation treatment cycle being available to a user or a clinician. There is no external or exterior means to adjust or control the device either prior to activation of the device or after the device is activated. Also, there are no internal control means that may be controlled through exterior communication with the device. In addition in the self-contained device of the present invention the source of power is preferably one or more internal batteries and there are no external sources of power.

It is preferred that the device of the first aspect of the present invention is a one-shot or single use device that may only be used once and have no means of re-programming the electro-stimulation treatment cycle or re-initiating the pre-programed electro-stimulation treatment cycle. This means that after use even if the device is re-inserted into the vagina it will not operate. Micro-processing control means within the body of the self-contained device is programmed to deliver a single electro-stimulation treatment cycle per device.

The one-shot or single use may be imparted to a self-contained (as defined in relation to the other aspects of the present invention) electro-stimulation device through management of the internal battery. In general terms the battery may be selected to provide just sufficient power to the device to complete a single treatment cycle. In practice this is difficult and normally there will be a reasonable level of residual power in the battery power source of the device. The level of power required will vary from device to device and the nature of the pre-programmed treatment cycle. There may therefore be residual power in the battery after the device has been used for electro-stimulation. In addition if the treatment cycle is interrupted there will be residual battery power. Once the device has been used and prior to its disposal it is desirable that the battery power within the device is depleted and that the battery is essentially flat. Thus there is a need to prevent re-use of the device to ensure that this is a one-shot or single use device and a need to ensure that the device may be safely disposed. Thus in accordance with a further aspect of the present invention once a device has completed a treatment cycle of electro-stimulation or if such an electrostimulation cycle is interrupted during the treatment cycle the microprocessor within the device is programmed to control the device circuit in order to discharge any remaining power from the devices battery based power source. This discharge is controlled to ensure that no discharge of power occurs via the devices exterior electrode surfaces.

Thus in accordance with a fifth aspect of the present invention there is provided a single use self-contained muscle electro-stimulation device, which device comprises:
a) a device body,
b) at least two electrodes for delivery of pulsed electro-stimulation current to muscle,
c) at least one source of internal battery power, and
d) at least one internal control unit comprising means for generating and controlling the delivery of an electro-stimulation treatment cycle via the electrodes to muscle, the controlling means programmed to discharge any residual internal battery power on completion or interruption of the electrostimulation treatment cycle.

In a preferred embodiment of the fifth aspect the discharge of the battery is effected by the continuation of the pulsed treatment cycle but with isolation through microprocessor control of the device electrodes preventing any electrostimulation voltage from being applied across these electrodes. In a preferred embodiment of this aspect the device is activated through the removal of a battery tab, which passes from the exterior of the device and into the body of the device and preventing the battery contacts from making contact with the internal device circuitry. Removal of this battery tab allows the battery contacts to make appropriate contact with the circuitry so that power may be delivered to the internal circuit and microprocessor from the battery. It is preferred that the microprocessor within the device is programmed to deliver a treatment cycle upon having power delivered from the battery and preferably after completion or interruption of the treatment cycle to continue to load the battery until all of its power is depleted such that the battery is discharged and of no practical use; effectively fully discharged. Thus in a preferred embodiment the device comprising internal battery is activated and power is initially withdrawn from the internal battery for the electrostimulation treatment and then continues to be drawn from the internal battery to deplete and discharge it. In a preferred embodiment the period from activation of the device to completion of internal battery discharge comprises the treatment period plus 1 hour or less discharge period, more preferably 45 minutes or less and most preferably 30 minutes or less. Ideally a battery is selected that has sufficient power to deliver the treatment cycle and the shortest possible discharge period following completion or interruption of that treatment cycle. Preferably the battery will continue to deliver power once the device is activated for completion of the treatment cycle plus a minimum of 15 additional minutes for battery discharge following completion of that treatment cycle. Typically this will mean a total minimum battery life of approximately 45 minutes from activation of the device for a 30 minute treatment cycle. It is to be understood that the fifth aspect of the present invention may be used in combination with one or more of the other aspects of the present invention disclosed herein.

In all aspects of the present invention the target output current is preferably for delivery to the muscles of the pelvic floor either for treatment or exercise of the pelvic floor.

The general principle design and methods of operation of a preferred device according to all aspects of the present invention are as follows. The device typically comprises a body preferably of foam based material with electrodes at or on the surface of the device body. The device body is preferably made of compressible foam so that it may be easily compressed prior to insertion into the vagina and once in-situ is able to expand pushing the electrodes into contact with muscle to be exercised. Being flexible and compressible in nature when in-situ the foam body may change shape under applied pressure to conform to surfaces in contact with it. A further benefit of the foam body is that it is light in weight and is relatively easy to retain in the body once inserted due to this light weight and the expansion/contact of the foam body with the muscle. Within the interior of the foam body is located all of the components of the device required to operate and control the device during use; these typically comprise a power source and the associated circuitry, typically on a PCB required to control and deliver a pre-programed electro-stimulation treatment cycle via the electrodes to exercise the muscle. The device has no exterior controls or switches and may simply have a pull tab arrangement associated with the interior power source e.g. battery, which may be removed from the device prior to insertion into the vagina, to allow the battery to engage with and deliver power to the control and stimulation circuitry within the device. The preferred device is of a size and shape that it may be completely inserted into the vagina and to allow closure of the vaginal introitus, with no parts of the device being exposed outside of the body. There may be a small cord at the distal end of the device, which passes out through the vagina to aid withdrawal from the vagina after the treatment cycle is completed. The present invention brings new features and functions to this general design and is preferably used with this general design. However, the features and functions of the present invention may be used with other designs of electro-stimulation devices known in the art.

In a conventional device a voltage is typically selected to deliver a treatment output current to the muscle during electro-stimulation. Typical voltage values are based on the typical treatment parameters determined from clinical practice. There is little if any variation from these values during use. In contrast the devices and methods of the present invention are designed to be capable of providing variable voltages automatically and preferably within a self-contained device, with the objective of ensuring that as often as possible during an electro-stimulation treatment cycle the muscle receives a target output current for electro-stimulation.

In a conventional device the power source is typically external to the device and power levels for delivery during the treatment cycle may be determined and/or adjusted by user/clinician control means. With a self-contained device in accordance with the present invention such intervention is not possible and is not required. In the present invention there is a return path through the muscle and device through which may be measured a return path voltage. Thus along this return path there is located within the device a means for measuring the return path voltage. It is preferred that the means for measuring the return path voltage comprises one or more resistors. Thus during operation of the device at the applied voltage level the current passing through the user's muscles creates a small voltage across this return path resistor and this is proportional to the current applied and impedance of the users muscle. Thus in all aspects of the present invention it is preferred that the means for measuring the return path voltage comprises one or more resistors in combination with means for measuring the voltage across the one or more resistors. It is preferred that the resistance of the resistor is selected to enable a return path voltage to be measured that is within the range of 0.25 to 0.75 times the battery voltage in the device. This range provides optimum sensitivity in ensuring meaningful adjustments to output voltage. This is particularly preferred when the microprocessor is an 8 bit microprocessor. The lower the resistor value, the lower the voltage (and the higher the resistance, the higher the voltage). The value of the resistor needs to be as small as possible so as not to influence the feedback. If a poor resistor value is selected the feedback voltage could be out of the measurement range of 3 volts maximum (where dictated as such by the battery voltage), or could be so small as to give poor resolution. An 8 bit processor only has 255 levels to measure so has limited resolution if poor resistor value chosen. It is preferred that the resistance of the resistor used for the measurement of return patent voltage values is from 10 to 100 ohms, preferably 20-50 ohms and most preferably 30 to 40 ohms.

This return path voltage is measured and this is proportional to the current passing through the muscle at the applied voltage. This measured return path voltage may be compared to the known voltage required to deliver a desired target output current. The relationship between these two voltages is then used if necessary by a control unit to provide an adjusted signal to a voltage control unit to increase or decrease the output voltage level for subsequent electro-stimulation in order to deliver the target current output to the muscle. This measurement, calculation and adjustment may be carried out at any number of pulses during an electro-stimulation treatment cycle. Within a treatment cycle there may be regular sequences of pulses with periods of no stimulation between each sequence and there may be more than one set of pulse frequencies. Pulses at different frequencies may be at different intensities. These measurements may be undertaken during each pulse sequence and at one or all pulses in each pulse sequence or they may be taken at alternate sequences of pulses or other variations. If more than one pulse frequency is used the measurements may be taken at one or more of the pulse frequencies or at all of the pulse frequencies. In a preferred embodiment of the present invention this measurement, calculation and adjustment is undertaken at each and every pulse in the electro-stimulation treatment cycle. One preferred set of pulse frequencies is as described in U.S. Pat. Nos. 6,236,890 and 6,865,423, the whole contents of which are hereby incorporated by reference.

Thus in a preferred embodiment of all aspects of the present invention the microprocessor based control means is programmed to undertake measurements of various parameters, to perform calculations and/or comparisons based on these measured parameters and/or fixed parameters and to control adjustments to voltage levels at each and every pulse based on these measurements. This means that for subsequent pulses the voltage level will be the adjusted or non-adjusted voltage level from the preceding pulse.

In embodiments, the target value for return path voltage may be a root mean square voltage, and the target (pulsed) output current may be a root mean square current. When an electro-stimulation pulse is delivered to muscle it has a finite duration and it has been found that through the duration of the pulse the impedance in the muscle under electro-stimulation changes. This is demonstrated in FIG. 2, where it can be seen that the return path voltage after an initial peak decreases or decays in a distinctive way as the pulse progresses to completion. This is the typical profile for an electrostimulation pulse. The initial high peak value indicates relatively low muscle resistance. As the muscle starts to work under the action of electro-stimulation the muscle resistance increases and the return path voltage decreases. At each point in the pulse profile the current imparted to the muscle will vary in proportion to the impedance of the muscle and the voltage. In one embodiment of the present invention it is preferred that the target pulsed output current for the device is determined by taking into account this pulse profile. In a preferred embodiment the device is configured and programmed to accommodate the pulse profile for the return path voltage in order to calculate a return path voltage value for use in adjusting the output voltage for subsequent electro-stimulation. Thus in a preferred embodiment the return path voltage is the Root Mean Square return path voltage of the whole electro-stimulation pulse. This may be represented using the following equation:

$$\text{Volts}_{RMS} = \sqrt{(V_1^2 + V_2^2 + V_3^2 + V_n^2) \div n}$$

In a preferred embodiment the RMS return path voltage is determined for value of n from 6 to 100, more preferably for values of n from 8 to 50, more preferably 8 to 20, more preferably 8 to 16 and most preferably 12. The voltage values for n being taken at a series of regular time intervals during the pulse and used to calculate RMS return path voltage. This RMS return path voltage is directly proportional to the current delivered to the muscle through the following relationship:

$$\text{Current}_{RMS} = \text{Volts}_{RMS}/\text{Resistance}.$$

Thus in a preferred embodiment of the present invention the output voltage is set to deliver $\text{Current}_{RMS}$ as the target pulsed output current. The $\text{Volts}_{RMS}$ is determined for each pulse and this value is used to adjust the output voltage to deliver $\text{Current}_{RMS}$. These measurements preferably being determined by the microprocessor and suitable adjustments being communicated to the voltage control unit in order to deliver the required output voltage. $\text{Volts}_{RMS}$ may be determined for the whole or part of a pulse. When it is determined for part of a pulse it is preferred that it is determined for the initial period of the pulse equating to 50% or less of the pulse duration. In a preferred embodiment when $\text{Volts}_{RMS}$ is determined for part of a pulse it is determined for the first 50-60 µs of a pulse. It is preferred that $\text{Volts}_{RMS}$ is determined for the whole electro-stimulation pulse.

With the devices of the present invention it is preferred that the electronic circuit and control is as small and as compact as possible especially when in a self-contained device. In this regard it is desirable to use as small a processor as possible and this usually means lower levels of processing power e.g. an 8 bit processor as opposed to a 16 bit processor. The lower levels of processing power has the advantage that less power is required and smaller less powerful batteries may be used in for example a self-contained device. However, reduced processing power does mean that it is difficult to undertake complex measurements and calculations, especially within the time frame of these devices with typically very short electro-stimulation pulse durations. One challenging aspect is the determination and use of $\text{Volts}_{RMS}$ for output voltage adjustment.

It has been found that this challenge may be accommodated by measuring return path voltage at a specific point in time in a pulse. It has been found that measurement at that specific point in time is an acceptable alternative to measuring $\text{Volts}_{RMS}$ and ensuring that output voltage delivers the target output current. It is preferred therefore that that return path voltage is determined at a certain point in the electro-stimulation cycle and/or muscle contraction during an individual electro-stimulation pulse. The muscle starts contracting at the start of the returned pulse (see FIG. 2). It is preferred that all measured or calculated feedback parameters of the device are determined at or in relation to this point in the muscle contraction. As will be discussed in more detail later with reference to the Figures, in the present invention it is preferred that the return path voltage is measured at a particular point during the pulse after the initiation of the muscle contraction. This measurement is preferably taken between 20 to 40 μs after the muscle has started to contract, preferably 25 to 35 μs, more preferably 27.5 to 32.5 μs and most preferably at or about 30 μs. It has been found that readings within these ranges and preferably at 30 μs after the muscle has started to contract provide the most reproducible and accurate measurement of the return path voltage for the determination of the subsequent adjustment of output voltage to deliver the target output current and calculation of relative muscle impedance. It has been found that the time versus voltage profile of the current waveform pulse for any group of users differ considerably making it difficult to measure a comparable level between users. It has been found that the initial rise at the start of the pulse and at rollover vary in an ad hoc fashion even for the same user during an individual electro-stimulation treatment event. Measurement of the pulse peak level has been found to be problematic because within the pulse profile it is a relatively transient point producing a small target to measure and depending on muscle characteristics can produce different pulse peak voltages. It has been found that measuring within the indicated ranges and preferably at or around 30 μs surprisingly provides the optimum point to measure a single return path voltage, which may then be used in calculating the adjustment needed to the output voltage so that the current delivered to the same or different users is effective. Although not wishing to be bound by theory it is believed that at this point the muscle is stable after initial changes at the start of a pulse. At the start of a treatment pulse the muscle fibers contract drawing a surge of current, this then reduces as the muscle stabilizes and it is in this more stable environment that it has been determined readings of return path voltage should be taken. This is also preferable to measurement later or at the end of a pulse, where the signal is low/weak, and therefore the resolution of the measurement may be low. Thus it is preferred that no return voltage measurements are taken solely at or near the end of the pulse and that no current value is measured based in measurements solely at or near the end of the pulse. When the return path voltage of each and every pulse is measured it is preferred that this return path voltage is measured within the indicated ranges and preferably at or about 30 μs. In a further embodiment the return path voltage may be determined as an RMS value between the indicated ranges of 20 to 40 μs after the muscle has started to contract, preferably 25 to 35 μs and more preferably 27.5 to 32.5 μs.

The use of the measurement of return path voltage with the subsequent determination of adjustment for output voltage in accordance with the present invention may be undertaken with any device where a target output current is required. This includes the preferred self-contained devices of the present invention or more conventional devices.

It has also been found that the effective automatic operation of the devices of the present invention may also be impacted by a specific problem identified with self-contained devices that incorporate a battery as the power source when the battery voltage is being used as a reference. In these self-contained devices one typically desires to use relatively small, low voltage batteries as the power source, with the use of circuitry as herein described to boost this voltage to a desired power level for the electro-stimulation. These batteries may be rated at 6 v or less and typically are at 3 v or less, and may be as low as 1 volt, with circuitry in the device for boosting the device output voltage to 10V or more. However, in self-contained devices designed to deliver consistent, controlled and automatic operation these low energy batteries are problematic. One problem is that they have been found to exhibit significant variability in terms of performance from batch to batch or within a batch. A second problem is that they exhibit variable depletion characteristics during use. A further problem is that they also age with storage and this ageing is not predictable. Many problems stem from the fact that these small and low power batteries are usually designed to provide trickle power output over long periods of time, rather than bursts of current (such as the pulses of 100 mA proposed herein). These variables result in a situation that for any given self-contained electro-stimulation device the properties and condition of the battery especially its voltage are an unknown quantity as such devices may be used at varying points in time after their initial manufacture. In these circumstances using the battery voltage as a reference point based on a presumed voltage is problematic leading to incorrect adjustments to power levels and as a consequence the delivery of inappropriate output currents to an electro-stimulated muscle, with the consequence of delivering less effective treatment. An additional effect is that the precious battery power in such a self-contained device is not used effectively and may be squandered.

Thus in a preferred aspect of the present invention the devices and methods when self-contained and battery powered further comprise a battery management means and process. In the preferred embodiment this is achieved through use of a fixed voltage reference diode located within the power circuit and preferably located within the core control circuit. This reference diode may have any suitable fixed voltage. Preferably it is fixed at 0.6V. Other voltage references are available ranging from 0.6 to 5 volts and above. The fixed voltage reference may also be provided by an external diode or reference voltage. Preferably it is internal to the device.

The problem with variable battery voltage being used as a reference may be illustrated as follows for instance when the self-contained device is controlled by an 8 bit microprocessor. Such an 8 bit microprocessor measures items in numbers which are referenced to the battery voltage and measures up to values of 255. The analog to digital converter inside the microprocessor takes the battery voltage and divides by 255 to calculate its basic step size and provides the information required by the microprocessor in order to deliver an appropriate control signal to the voltage control unit within the device. When the microprocessor is measuring it starts with one step and compares to the voltage being measured, if they are not equal it adds another step and repeats until the value of the cumulative steps equal the voltage being measured. The value of the cumulative steps is returned to the microprocessor program to make a decision based on the value returned (value being 0-255).

If we consider for example a device set to measure a target 1 volt return path voltage for each pulse for adjustment of the output voltage. Two scenarios illustrate the problem. In the first a 3 volt battery will be referenced by the microprocessor as 3/255=0.012 volts. This is calculated @1 volt/0.012=83, therefore in this example the recorded level would be 83. In the second a 2.5 volt battery will be referenced by the microprocessor as 2.5/255=0.010 volts. This is calculated @1 volt/0.010=100, therefore in this example the recorded level would be 100. This illustrates the problems of measuring voltages with a variable battery; the value for return path voltage is variable depending on the actual voltage of the battery being used in the device.

Thus in the present invention in one embodiment this problem is preferably resolved through the use of a fixed reference voltage within the device. The reference voltage may be used to calculate the battery voltage or may simply be used to provide a meaningful value for the microprocessor to use. This allows the use of the reference voltage to more accurately measure the return path voltage level and to multiply this reading to a required value for the voltage control unit of the device as described below. Using this method the microprocessor values communicated to the voltage control unit of the circuit will change in line with the battery level as described in the following example in order to ensure that the voltage control unit receives the correct value to deliver the output voltage to achieve the target output current. The fixed reference voltage may be any point within the circuit that has a known voltage. In a preferred embodiment inside the microprocessor the reference voltage is provided by a diode fixed at 0.6 volts. Using the calculations described above, 0.6 volts at 3 volts would record a value of 50 in the microprocessor and 0.6 volts at 2.5 volts would record a value of 60 in the microprocessor. As there is now a reference guide to the battery level and a known reference voltage this can be used in a calculation for the microprocessor to more accurately deliver scale up values to the voltage control unit to attain the required power level in order to deliver the target output current more precisely.

In other words, the voltage across the diode is always known (a constant value of 0.6 volts). The microprocessor A/D converter's reference is the battery level (battery voltage/255), so as the battery level varies, the value returned for the known 0.6 volts therefore also varies. Because the diode voltage is known (constant 0.6 volts) the target feedback value can be scaled from this value.

With a target return path voltage of 1 volt and a reference of 0.6 volt, a multiplication factor of 1.65 (1/0.6) would be required to scale the measured value of the reference for a battery level to reach the target voltage. With a 3 volt battery the target for 1 volt would then be 83 (50*1.65). With a 2.5 volt battery the target for 1 volt would be 99 (60*1.65). The reference voltage is preferably measured during a pulse preferably towards the end of the pulse, more preferably at or greater than 35 μs into a pulse, more preferably at or greater than 40 μs into a pulse and most preferably at or greater than 50 μs into a pulse. This value (reference voltage plus scaling) is then used with the measurement of $Volts_{RMS}$ or the return path voltage at or around 30 μs to adjust the value for output voltage for subsequent electro-stimulation.

In a preferred embodiment the routine for compensating for battery voltage is undertaken for each and every electro-stimulation pulse from the device and preferably is undertaken before any subsequent electro-stimulation pulse is initiated.

In one embodiment the reference voltage is used to calculate the actual voltage of the battery at any given point in time and that value is used by the microprocessor to determine accurately the return path voltage and any other voltages measured by the device. This is in contrast to previously considered methods which address battery power, which typically are aimed at determining what amount of battery power remains, whether the battery remains viable and the like. In embodiments of the present invention, the actual value of the voltage of the battery is determined, by referring to the reference voltage.

It is preferred that the devices and methods of the present invention use both the output voltage adjustment mechanism based on return path voltage feedback measurements as described herein and the routine based on a reference voltage for compensation for battery power level as described herein in the same device and control circuit. It has been found that if these two features are combined in a self-contained battery powered device the consistency and effectiveness of the device and methods described herein are significantly enhanced.

In a further embodiment the return path voltage may be measured and the value may be used in combination with a circuit comprising a comparator and a preset value for return path voltage held in the microprocessor memory in order to adjust the output voltage delivered by the device. This may be an autonomous circuit to the microprocessor. The number held in memory for the return path voltage target is fed to one pin of the comparator and the return path voltage is fed to the other pin of the comparator. Because this feedback is not under microprocessor control the return path voltage measured is typically at or about the peak voltage of the electro-stimulation pulse. If the return path voltage is less than target then the comparator output is at status quo and the output voltage is increased in line with the program in the microprocessor and the output voltage may be increased. However, once the return path voltage exceeds the target voltage at the comparator the comparator will generate an output and this will be noted by the microprocessor. At this point the microprocessor will prevent any further increases in output voltage until there is no output signal from the comparator. The microprocessor may be programmed to check the output value of the comparator at regular intervals and may be and preferably is programmed to check the output signal from the comparator at each and every pulse. This technique using a comparator is not as accurate as the preferred embodiment of the present invention, which utilizes scaling with the A/D convertor in the microprocessor. This is because a comparator compares a reference to the value to be measured and returns 1 or 0. In preferred embodiments using scaling with the A/D convertor, whether the measured value is higher than a reference or not, the A/D converter returns a value measured. This allows several decisions to be made depending on the value returned, such as whether the value is equal to the reference, whether it is lower and by how much, and so on. Also, this comparator based feedback is unable to utilize the method described herein for accommodating battery level. Therefore whilst it is an embodiment of the present invention it is not a preferred embodiment.

With reference to the first and second aspects of the present invention it is preferred that the device and method are configured and carried out to deliver one or more of three further additional operating conditions. The device and method of the first and second aspect of the present invention in addition to operating under conditions designed to provide a constant target output current may include other additional periods of operation within the overall treatment cycle that are not fixed in a constant target current mode.

One such additional period of operation is commenced before the constant target output current treatment phase and may by referred to as an initial constant voltage phase. In this phase the microprocessor is programmed to operate the device at a constant voltage as opposed to operating at a variable voltage to deliver a constant target output current. In this constant voltage phase a target output voltage is set at a level below the treatment level, preferably at 15 volts or less, more preferably at 12 volts or less and most preferably at 10 volts or less. In this constant voltage phase the output voltage is measured by the device and if this is in variance with the target output voltage the output voltage for subsequent electro-stimulation is increased or decreased. In this constant voltage phase the voltage and current delivered to the user are low and this enables the muscle to experience and accommodate low level electro-stimulation before the treatment levels are experienced. This constant voltage phase may comprise a series of pulse trains. Preferably each pulse train lasts 2 seconds or less and most preferably 1 second or less. Within each train the pulses are interspersed with increasing inter pulse intervals, preferably at intervals from 8 to 500 ms. Preferably the pulse durations are identical and are in the range of 100 to 350 µs, preferably 100 to 300 µs and most preferably from 125 to 250 µs. preferably each train will contain from 2 to 20 pulses and most preferably from 4 to 12 pulses. Preferably this phase comprises a series of pulse trains and preferably the pulse train is repeated within the constant voltage phase to provide a total number of pulses from 20 to 200, preferably from 40 to 120 and most preferably from 60 to 100 pulses.

A further additional period of operation may be and preferably is commenced before the constant current treatment phase and after the initial constant voltage phase. This second phase may be referred to as a current ramp mode. During this phase the microprocessor is programmed for and now switches to a constant current mode and seeks to steadily increase the voltage from the voltage level at the end of the initial constant voltage phase up to the operating voltage required to deliver the target pulsed output current for the treatment phase. As with the previous constant voltage phase the return path voltage measurements of $Volts_{RMS}$ or the measurement at 30 µs may be and preferably are used to determine if the target output voltage has been attained. In this phase the target return path voltage is now at a higher level than the initial phase. This second phase is designed to allow the current delivered to the user to be ramped from the low level at the end of the initial phase to being close to or at the required target output current at the end of this current ramp phase. In essence the output voltage is increased at each and every pulse in this phase under return path voltage feedback until the target output current is attained. This current ramp phase may comprise a series of 1 second pulse trains. Within each train the pulses are interspersed with increasing inter pulse intervals, preferably at intervals from 8 to 500 ms. Preferably the pulse durations are identical and are in the range of 100 to 350 µs, preferably 100 to 300 µs and most preferably from 125 to 250 µs. preferably each train will contain from 2 to 20 pulses and most preferably from 4 to 12 pulses. Preferably this phase comprises a series of pulse trains and preferably the pulse train is repeated within the current ramp phase to provide a total number of pulses from 40 to 1000, preferably from 80 to 600 and most preferably from 260 to 280 pulses.

A further preferred operating condition is to include what may be referred to as means to detect contact of the device with the pelvic floor muscle. The device may be configured to expect to detect a certain range of return path voltages and these may be set at a relatively low level in the initial phase, at increasing levels during the current ramp mode and at a level relating to target output current in the treatment phase. These voltages are measured when the device is in contact with the pelvic floor. For safety the device may have mechanisms to turn off the device should voltages become too high as discussed herein. There is however a need to determine if the device is in contact with pelvic floor muscle before being fully activated and/or to turn the device down and/or off if it is removed from contact with the pelvic floor before completion of the treatment cycle. This may be achieved by selecting a low minimum level for the value of return path voltage; a level below that which would be expected for at least the initial phase of operation in contact with pelvic floor muscle. The microprocessor has this minimum value in memory and after the device is activated if the return path voltage is below this value determines that the device is not yet in contact with pelvic floor muscle and delays the treatment cycle until the device is in contact with the pelvic floor muscle or after an extended period deactivates the device and preferably discharges the battery. If the device is in contact with the pelvic floor this low voltage level for the return path voltage will not be seen or detected and the device remains in operation delivering the treatment cycle. If for any reason the device should be removed before the treatment cycle is completed the voltage across the return path will drop dramatically and below the low level set in the microprocessor memory and the device output will drop below treatment level or it will deactivate and preferably discharges the battery.

In one embodiment after activation through for example removal of a battery tab the electro-stimulation starts after a delay of up to 10 seconds to allow the device to be positioned in the vagina, then the microprocessor initiates electro-stimulation and proceeds through the treatment cycle preferably with the initial voltage phase and current ramp mode.

One embodiment of another aspect of the invention can provide an electro-stimulation device for delivering a target output current to muscle in contact with the device, which device comprises: a device body; at least two electrodes for delivery of pulsed electro-stimulation current to muscle; at least one source of power; and at least one control unit comprising means for generating a required output voltage to achieve a target output current, means for measuring return path voltage through the muscle and means for adjusting the output voltage required to achieve a target output current for subsequent electro-stimulation based on the measurement of return path voltage.

One embodiment of another aspect of the invention can provide a method of delivering a target output current for electro-stimulation of a muscle, comprising: providing an initial output voltage for delivery of the target output current for electro-stimulation; measuring a return path voltage from the electro-stimulated muscle; and where a return path voltage level indicates that the initial output voltage differs from that required for delivery of the target pulsed output current, adjusting the output voltage.

One embodiment of another aspect of the invention can provide a method for delivering a target output current to a muscle via pulsed electro-stimulation, which method comprises stimulating the muscle via pulsed electro-stimulation at an initial voltage level selected to deliver the target output current, measuring return path voltage within the circuit including the muscle at the initial voltage level, and based on the measured return path voltage adjusting the voltage level of subsequent electro-stimulation to deliver the target output current level to the muscle.

One embodiment of another aspect of the invention can provide a method for measuring the relative impedance within a circuit comprising muscle, which method comprises applying an output voltage to a muscle via at least two electrodes forming a circuit with the muscle, measuring the return path voltage within the circuit through the electro-stimulated muscle and comparing the applied output voltage to the return path voltage to calculate a relative impedance value for the circuit comprising muscle.

In embodiments, the steps of measuring and adjusting the output voltage are undertaken during an electro-stimulation event, or during a cycle period during the event. These steps may be undertaken during a single pulse. Measurements and adjustments may be carried out on each and every electro-stimulation pulse.

The return path voltage within the circuit may be determined as a root mean square voltage across the whole of at least one pulse. The return path voltage within the circuit may be determined (e.g. as a root mean square voltage) across at least one part of at least one pulse.

One embodiment of another aspect of the invention can provide a method of delivering a target pulsed output current for electro-stimulation of a muscle, comprising providing an initial output voltage for delivery of the target output current for electro-stimulation; measuring a return path voltage from the electro-stimulated muscle; and where a return path voltage level indicates that the initial output voltage differs from that required for delivery of the target pulsed output current, adjusting the output voltage, wherein the step of measuring the return path voltage comprises measuring a voltage level from an initial decay period of a returned electro-stimulation pulse.

One embodiment of another aspect of the invention can provide a method of delivering a pulsed output current for electro-stimulation of a muscle, using a power supply for which an output value is varying, the method comprising: providing an initial output voltage for delivery of the output current for electro-stimulation; measuring a return path voltage from the electro-stimulated muscle; and providing a further output voltage for delivery of the output current for electro-stimulation, wherein the step of providing the further output voltage comprises modifying the output voltage in dependence upon a comparison of the output value of the power supply with a reference voltage.

Further aspects of the invention comprise computer programs or computer program applications adapted, when loaded into or run on a computer or processor, to cause the computer or processor to carry out a method according to the above described aspects and embodiments.

Throughout this description reference is made to treatment regimen, event and cycle. It should be understood that the devices and methods of the present invention are not restricted to devices and methods of treatment of muscle but may also be used for the exercise of such muscle when there is no underlying medical condition associated with that muscle requiring treatment in the clinical sense. Thus in all aspects of the present invention where the context suggests a treatment regimen, event or cycle these terms may be replaced with exercise regimen, event or cycle. In these embodiments the devices and methods may be used exclusively for muscle exercise purposes. It is of course within the scope of the present invention to combine muscle treatment with muscle exercise.

In the description of embodiments of the present invention, processors and/or controllers may comprise one or more computational processors, and/or control elements having one or more electronic processors. Uses of the term "processor" or "controller" herein should therefore be considered to refer either to a single processor, controller or control element, or to pluralities of the same; which pluralities may operate in concert to provide the functions described. Furthermore, individual and/or separate functions of the processor(s) or controller(s) may be hosted by or undertaken in different control units, processors or controllers.

To configure a processor or controller, a suitable set of instructions may be provided which, when executed, cause said control unit or computational device to implement the techniques specified herein. The set of instructions may suitably be embedded in said one or more electronic processors. Alternatively, the set of instructions may be provided as software to be executed on said computational device.

DESCRIPTION OF THE DRAWINGS

For a better understanding of the invention, and to show how the same may be carried into effect, reference will now be made, by way of example, to various specific embodiments of the invention as shown in the accompanying diagrammatic drawings, in which.

DETAILED DESCRIPTION OF THE INVENTION

Figure 1:
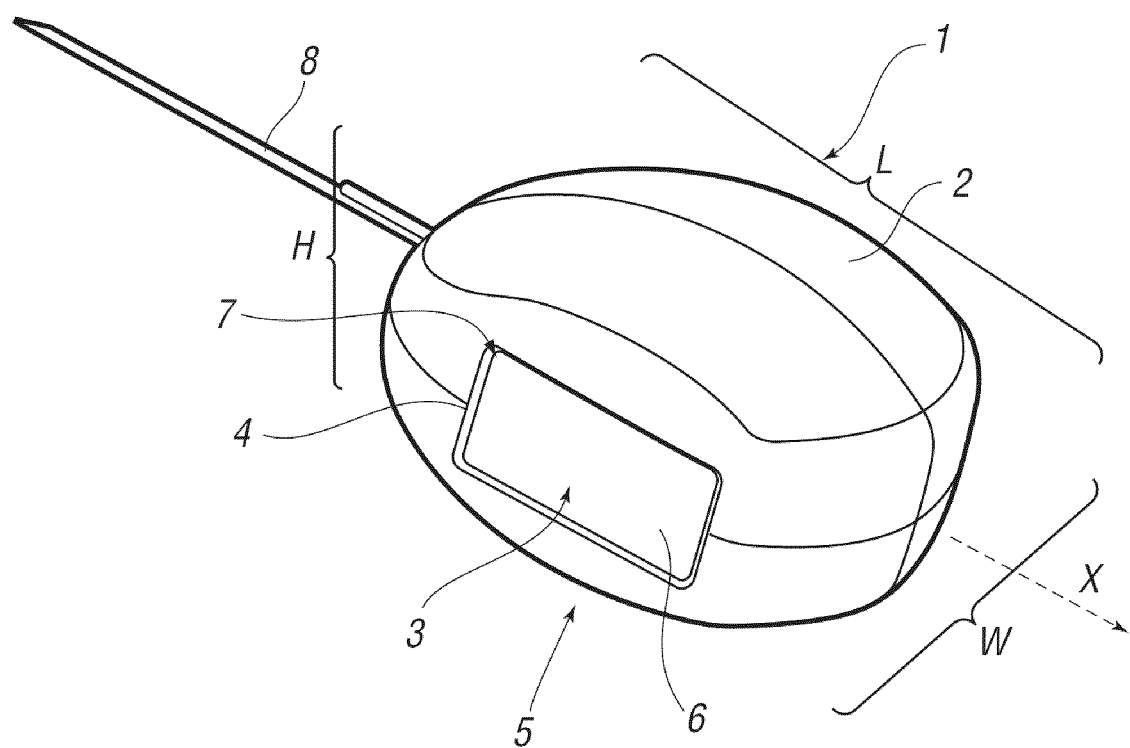
FIG. 1 (a) shows in perspective view of a preferred form of electro-stimulation device or device for measuring impedance according to the present invention.

Referring to FIG. 1 a self-contained electro-stimulation device (1) is shown in the non-compressed, fully expanded state. The device (1) has a body (2) which has been constructed from bio-compatible resiliently compressible foam. Electrodes (3 and 3' not shown) emerge from within the body (2) of the device and are located at the surfaces (4 and 4' not shown) on sides (5 and 5' not shown) of the device (1). The electrodes (3 and 3') are relatively flat. In this particular embodiment the electrodes (3, 3') are in communication with the internal components (not shown—see FIG. 3) of the device (1) through internal conductive paths. They pass from within the device (1) to provide electro-conductive surfaces (6 and 6' not shown) that are located in approximately the same plane as the surfaces (4, 4') of the sides (5, 5') of the device. The main body of the flat electrodes (3, 3') are located below the surface (4, 4') of the body (2) within a hollow cavity (not shown) within the body (2) of the device (1). The surfaces (6 and 6') of the electrodes (3, 3') appear through these openings (7 and 7' not shown) of the body (2). In one embodiment the electrodes (3, 3') may be surface mounted on the body (2) of the device (1); in this embodiment the surface mounted electrodes (3, 3') may be in contact with conductive paths that communicate with the interior of the body (2). The interior components of the device (1) are not shown in this Figure but are totally enclosed within the device body and are described in more detail below. The device (1) has a string cord (8) which is attached to the device and is used solely for removal of the device. The cord (8) may be made of string or similar materials, plastic materials or for example bio-compatible metal. The device has no external means for controlling or adjusting the device electronics located within the interior of the device body, which fully encloses these device electronics save for the electrodes at the device surface. All of the devices circuitry measurement, control and power components are located within the interior of the device and are inaccessible to the device user. Not shown in this figure is a tab that is inserted into the device body, preferably at the cord end of the device. This tab isolates the internal battery from the measurement and control circuits within the device body. In order to use the device and to activate the measurement and control circuitry this tab is removed enabling the battery to engage with and deliver power to the measurement and control circuitry. Preferably once removed the tab may not be reinserted into the device.

The dimensions of the device (1) which, in the non-compressed state, are such that the length (L) is greater than the width (w), which is in turn greater than the height (h). This device (1) when viewed in cross-section along the axis of insertion (X) has a non-uniform symmetrical cross-section. This non-uniformity means that the device (1) is less prone to rotation or displacement relative to the axis of insertion (X) during use of the device (1). The device (1) has no sharp edges whilst having clearly defined surfaces that are connected to each other by gently curving regions. The compressible properties of the device (1) ensure resilient contact with the muscles of the pelvic floor during use, its overall dimensions and shape, coupled with the smooth curvature of communicating surfaces, enables the device (1) to be easily and comfortably inserted during use, whilst at the same time limiting or preventing unwanted rotation and displacement during use. The shape and material properties of the device body are such that it is able to be compressed, flexed and change shape when in situ to conform to pressure applied by the interior surfaces of the vagina as they move; such movement especially occurring when the user is mobile.

Figure 2:
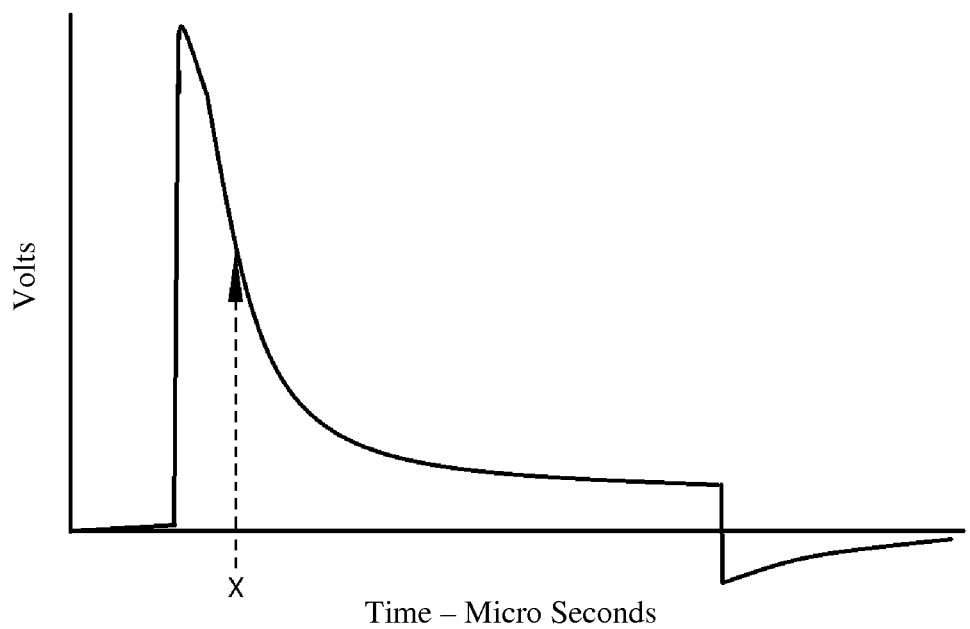
FIGS. 2 and 2(a) show a recorded electro-stimulation pulse delivered to a muscle demonstrating the shape of the waveform produced from an individual with the preferred measurement point indicated at 30 μs and also the principles for RMS measurements.
Figure 2A:
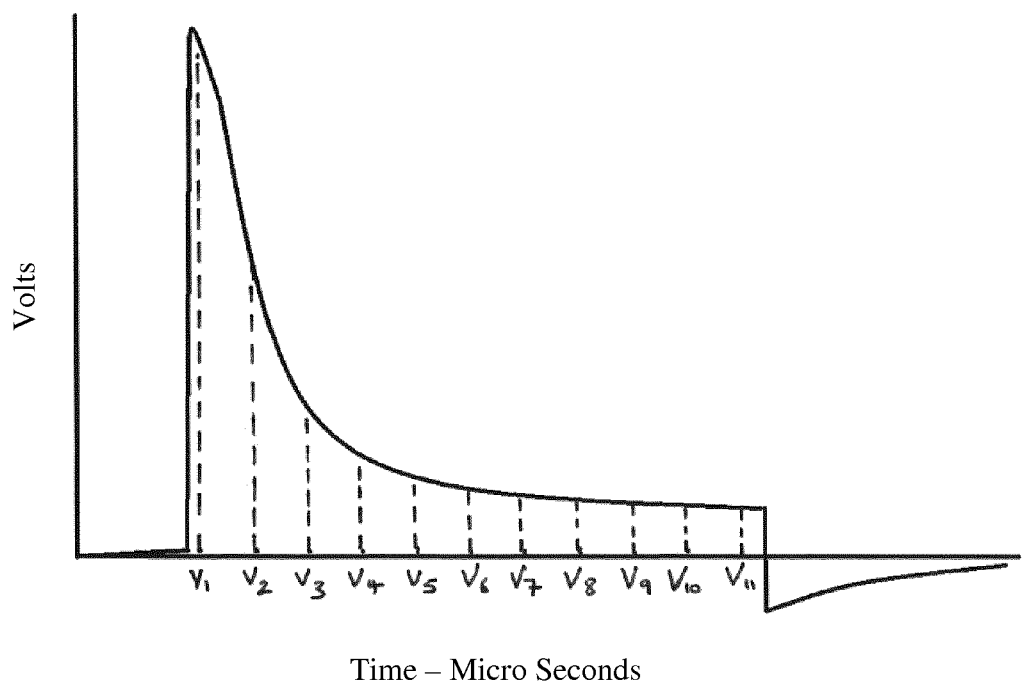

Referring to FIG. 2 a typical single pulse profile returned after being delivered from an electro-stimulation device to tissue according to the present invention, is shown indicating at point X the preferred point at 30 μs for measurement of the return path voltage, for use in the adjustment of the devices power level for delivery of the target output current. Referring to FIG. 2(a) the same single pulse profile is illustrated with regular spaced voltage measurements $V_1$ to $V_{11}$ for use in calculating Volts$_{RMS}$.

Figure 3:
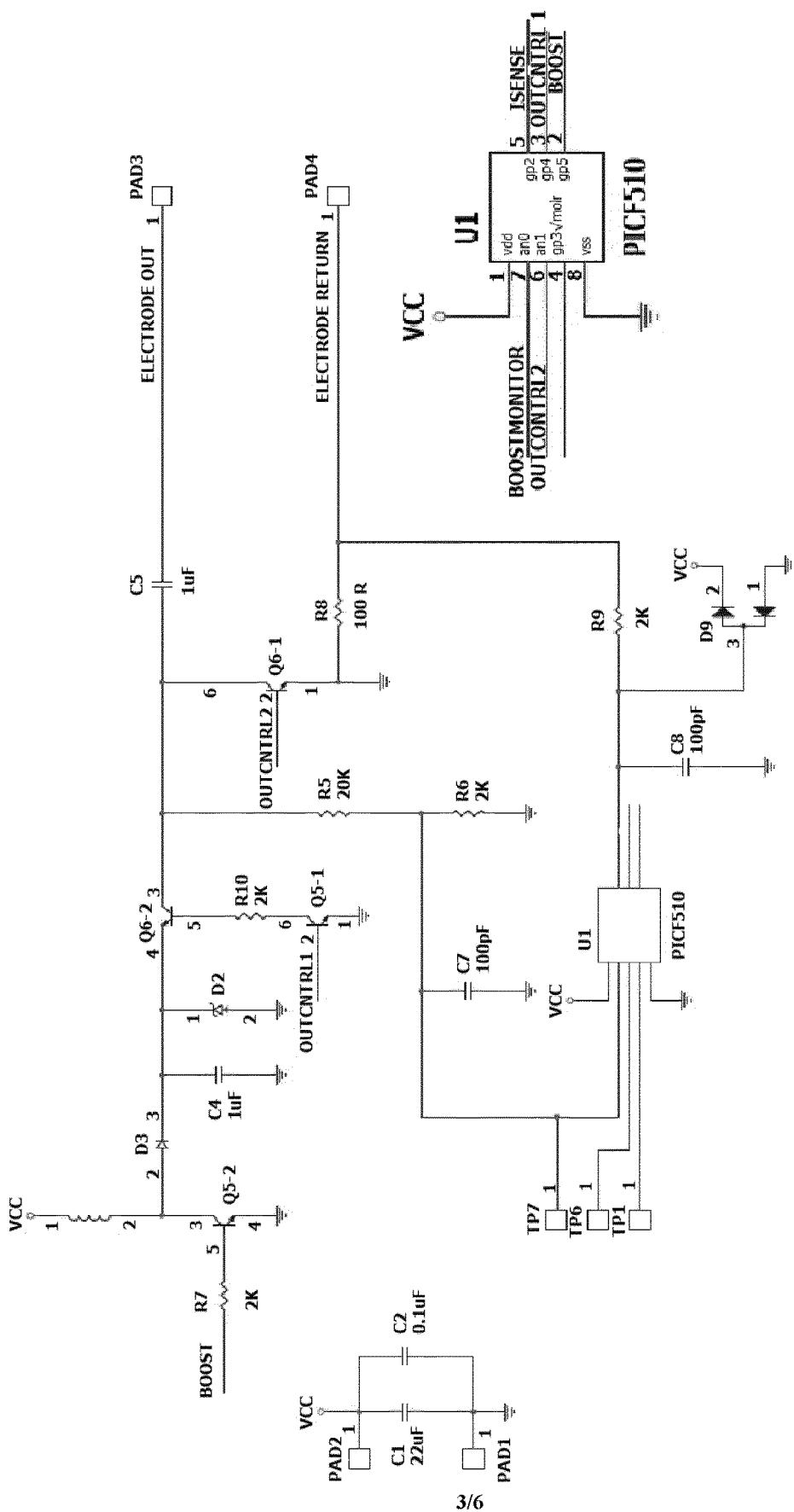
FIGS. 3 and 3(a) show a schematic of a preferred circuit for use in the electro-stimulation device or impedance measurement device of the present invention with highlighting of key components to aid description.
Figure 3A:
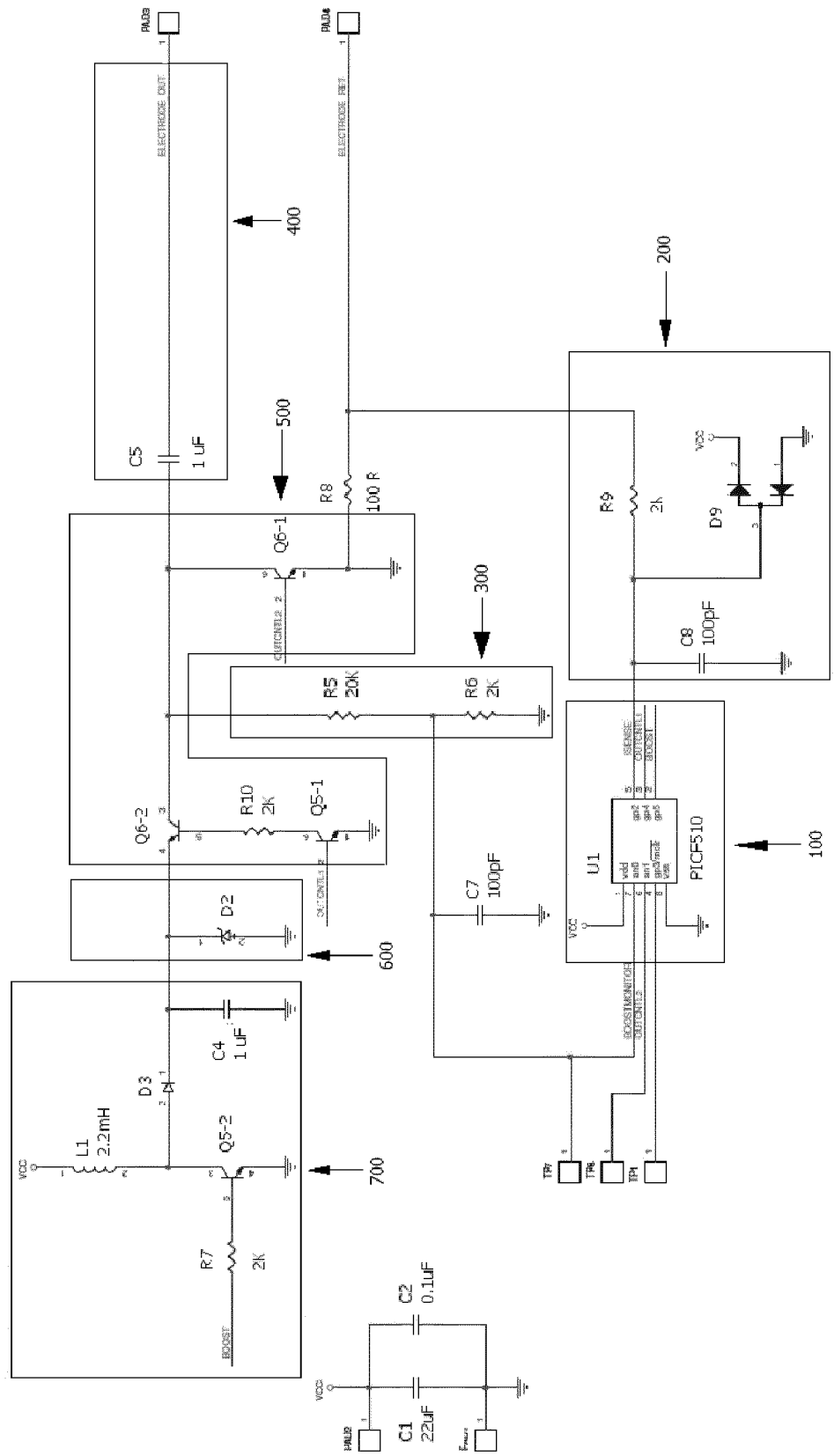

Referring to FIGS. 3 and 3a, the key components of a preferred circuit for use in the electro-stimulation device or impedance measurement device of the present invention are illustrated. These key components comprise: a microprocessor control unit (100), a return path voltage sensing circuit (200), a treatment voltage sensing circuit (300), a DC block (400), an output switch (500), a limit (600) and a voltage control unit (700). It is preferred that the device of the present invention comprises as a minimum a microprocessor control unit (100), a return path voltage sensing circuit (200), an output switch (500) and a voltage control unit (700). It is most preferred that the device of the present invention comprises all these circuit components.

The key components in FIGS. 3 and 3(a) are as follows:

| | |
|---|---|
| 700 | |
| L1 | inductor |
| R7 | resistor |
| D3 | diode |
| Q5-2 | NPN/NPN transistor |
| C4 | ceramic capacitor |
| 600 | |
| D2 | 30 volt Zener diode |
| 500 | |
| Q6-2 | NPN/PN transistor |
| Q6-1 | NPN/PN transistor |
| Q5-1 | NPN/NPN transistor |
| R10 | resistor |
| 400 | |
| C5 | ceramic capacitor |
| 100 | |
| U1 | Microprocessor |
| 300 | |
| R5 | resistor |
| R6 | resistor |
| 200 | |
| C8 | ceramic capacitor |
| D9 | Schottky Diode |
| R9 | resistor |
| C1 | ceramic capacitor |
| C2 | ceramic capacitor |
| R8 | ohm resistor |

The complete operation of the circuit is run by the microprocessor control unit (100). This comprises a microcontroller complete with A/D measurement inputs of battery voltage and the return path voltage. These inputs allow the microcontroller to set the correct output voltage to ensure that the target output current is delivered and maintained. The microprocessor also controls various other parameters for the electro-stimulation treatment cycle such as pulse profiles, pulse frequencies, pulse sequences, pulse intensity and pulse duration of the output pulses. The pulse frequencies and sequences are preferably as per those described in patent ref WO97/47357 and U.S. Pat. No. 6,865,423 or they may be any other suitable patterned stimulation programme. The microprocessor is preferably an 8 bit processor. The microprocessor is programmed with a target return path voltage; this is proportional to the target output current and the return path voltage is used to adjust the output voltage to deliver the target pulsed output current. As previously stated the microprocessor controls the pulse duration for the electro-stimulation treatment pulses. The microprocessor generates a Pulse Width Modulated (PWM) square wave to generate a variable increased voltage (the treatment voltage) via communication with the voltage control unit (700). The microprocessor (100) measures the treatment voltage via the treatment voltage sensing circuit (300). The microprocessor (100) measures the return path voltage via the return path voltage sensing circuit (200) and compares this measured voltage to the programmed target output voltage value in the microprocessor and this comparison is used to adjust the PWM signal to the voltage control unit (700) in order to adjust the output voltage power level for a subsequent treatment pulse to a level required to achieve the target pulsed output current. The microprocessor (100) also monitors the voltage levels being delivered to the user and via use of a pre-programed algorithm caps the output voltage level at a predetermined maximum level to prevent excessive voltage if for example the resistance in the circuit is too high. The microprocessor (100) is capable of recording all data measured and calculated within the device for future analysis. The microprocessor (100) also times and controls the length of electro-stimulation bursts and overall duration of the treatment.

The voltage control unit (also referred to as voltage boost) (700) receives PWM signal pulses from the microprocessor (100) to control the power level delivered to the user. The battery output, which is typically 3 volts may be and preferably is boosted via the voltage control unit (700) to a maximum of 35 volts from the limited power available in a button cell battery. The PWM signal from the microprocessor (100) drives a transistor Q5-2 and grounds an inductor L1. When grounded the inductor L1 draws current and generates an electrical field proportional to the current (derived from the width of the PWM on time). When the transistor Q5-2 does not conduct, the magnetic field collapses generating a voltage in the inductor L1. This voltage is higher than the battery voltage and proportional to the PWM signal. The bigger the ON to OFF ratio in the signal the higher the voltage generated in inductor L1. The PWM signal is approx. 50 kHz. This high frequency ensures that the battery does not have to supply current for a long period of time. The PWM pulse widths are between 1 µs and 10 µs, depending on the instructed duty cycle. Each PWM pulse draws 100 mA for a very short period of time dependent upon the PWM ON cycle. This voltage flows through the diode D3 and is stored by the capacitor C4. The diode D3 acts as a one way valve and stops the charge on the capacitor C4 from leaking away when the boosting signal is not being generated by the microprocessor (100). The whole operation of boosting the battery voltage takes place prior to the initiation of every treatment pulse and lasts for typically 10 mS.

For the avoidance of doubt, it is noted here that the treatment pulses are distinct from the pulses of the PWM signal. The treatment pulses are the pulsed current used for the electro-stimulation of the muscle via the electrodes, as described herein, with pulses for example at 250 µs width, and at intervals of 8 mS to 500 mS.

The circuit also comprises a voltage sensing circuit (300). This component is used to provide feedback to the microprocessor/controller (100) and is used to sense the treatment voltage level. Voltage measurement is provided by resistors R5 & R6, & C7 these act as a ladder divider and divide the treatment power level by a factor of 10. This is needed because the treatment power level is much higher than the battery voltage. So a desired maximum power level of 20 volts is divided down to 2 volts for the microprocessor (100) to measure. This is measured approximately 40 µs after the start of the treatment pulse (After Current feedback) C7 acts as a filter to ensure a smooth level to be measured. This voltage measurement is used in conjunction with the return path voltage feedback to limit output voltage in case of high user impedance in the circuit and is an optional but preferred safety feature. Thus the devices of the present invention preferably comprise a voltage sensing circuit.

Capacitor C1 is a reservoir which supports the battery during boost, preventing battery voltage droop. Capacitor C2 filters high frequency interference from the microprocessor.

The device circuit also preferably comprises a fallback voltage limiter which is only used in the case of a failure in feedback or software (600). In a preferred embodiment this takes the form of a zener diode D2, which is not used under normal conditions. Its function is to limit the maximum treatment level of the device to 30 volts. The power level required for the preferred electro-stimulation device of the present invention is typically from 10 to 20 volts, more preferably 10 to 18 volts and most preferably 12 to 18 volts, with a specified maximum of around 26 volts. Any failure in feedback or software that could create an undesirable output voltage level is restricted to 30 volts by the zener diode, thus limiting the output voltage delivered to a user to a totally safe level.

The device circuit also comprises a return path voltage sensing component (200), which preferably uses measurements of return path voltage taken at 30 µs into the electro-stimulation pulse. This component is used to measure the return path voltage during use of the device which at the known resistance of the resistor used in the circuit is proportional to the current being supplied to the muscles of the user. This return path voltage is monitored to ensure that the user is receiving the required target output voltage and thus the target pulsed output current and is an important feature of the present invention. This measured return path voltage is compared to the target for return path voltage related to the output voltage required to deliver the target pulsed output current and the power level boosting signal from the microprocessor (100) is adjusted accordingly to ensure the output voltage of operation is adjusted to deliver the target pulsed output current. This measurement is undertaken by use of resistor R8 and optionally with R9 & C8. The return path current from the user flows through sense resistor R8. The current through this resistor is exactly the same as through the pelvic floor muscle of the user. The current is related to the return path voltage according to the formula I=V/R. The return path voltage across this resistor is determined preferably for each pulse. Resistor R9 and capacitor C8 are optional and provide a limiting and filter function to ensure that static, body movement and DC potential due to muscle activity and chemistry do not influence the .return path voltage. The large value of R9 limits any external voltages and protects the microprocessor (100), preventing damage and the effect of excessive measurement values. In combination with C9 it also forms a shaping filter, this rounds and softens the shape of the return path voltage. The return path voltage is measured by R8 30 µs after start of a treatment pulse. This gives a relatively stable and consistent place to measure the return path voltage for output voltage adjustment. Diode D9 is used to prevent excessive voltages due to static or failure of the current sensing components. D9 is effectively two Zener diodes back to back and limits surges from any polarity.

The circuit also comprises an output switch (500). This section of the circuit switches the operation voltage level to the user and under control by the microprocessor creates the output pulse waveform for the treatment cycle. After each pulse the electrodes (3, 3') of the device (1) are grounded. This creates the asymmetrical waveform and grounds the user between pulses to remove any DC potential from the skin. The capacitor C5 (400) ensures that there is no DC to the user in normal use and prevents DC being applied in a fault condition should the output switch (500) be faulty. This output switch (500) switches the stored output voltage to the user from capacitor C4. It consists of an NPN and PNP pair of transistors Q5-1 & Q6-2. The microprocessor (100) switches on Q5-1, which in turn switches on Q6-2. These transistors operate in this fashion because the switched power level is higher than the battery voltage and could not be switched by a single transistor; therefore preferably the output switch (500) comprises at least two transistors and preferably at least one NPN and at least one PNP transistor. Q6-1 transistor grounds the output capacitor C5 until a pulse is delivered to the user. This ensures that there is no voltage applied to the user before a pulse, and also reverses the charge on capacitor C5 to deliver a negative waveform to the user and also zeroes the charge on the capacitor before each pulse to ensure that they are all the same size. In operation Q6-1 is preferably always switched on until 1 μs before a treatment pulse is generated then it is switched off. When Q6-1 is switched off transistors Q5-1 & Q6-2 are switched on for the duration of the pulse then they are switched off. After the treatment pulse there is a 1 μs delay and then transistor Q6-1 is switched on to ground capacitor C5.

The VRef is a reference measurement of the battery level after the desired power level has been delivered via the voltage control unit (700). Inside the microprocessor (100) is a reference diode (not shown—see FIG. 5) that can be measured by the microprocessor (100). This is preferably measured at 50 μs or later after a treatment pulse is initiated. This gives an accurate indication of battery voltage after the boost is completed as described above.

In more detail, the outputs of the microprocessor 100 (U1 as shown in FIG. 3) are as follows:
OUTCNTRL1—output control—this switches the boosted voltage to the user (OUTCNTL2 will be off when OUTCN-TRL1 is on);
OUTCNTRL2—this switches DC block capacitor C5 to 0 volts, generating a negative pulse (OUTCNTRL1 will be off);
BOOST—this is the PWM signal, instructing the voltage control unit (700) to boost from 3 volts to treatment level as described above;
BOOSTMONITOR—this is the voltage feedback from the boosted signal, as described above regarding the treatment voltage sensing circuit 300; this is used as described above in conjunction with current feedback to control output; and
ISENSE—this is the current feedback from the user, as described above regarding the return voltage sensing circuit 200.

In a specific embodiment, the whole circuit shown in FIGS. 3, 3*a* may generally be operated as follows. At switch on, there is a 10 second delay. Then the device begins electro-stimulation in the initial constant low voltage mode. The microprocessor (100) is programmed to generate a low voltage (below the treatment power level) and starts the treatment at this low voltage and uses voltage feedback to maintain an output voltage of 10 volts. After this first phase the microprocessor (100) switches to the current ramp mode with increasing voltage to reach the voltage required to deliver the target output current for treatment. On completion of the current ramp mode the device moves into the treatment cycle. In this phase the return path voltage is measured and is compared to a target return path voltage related to the target output current value stored in the microprocessor (100) to determine the output voltage required to deliver the target output current during at least one subsequent electro-stimulation pulse and to do this at each and every pulse to ensure that the target output current is delivered to the users muscles. After this point the device continues to operate in current feedback mode via measurement of return path voltage for the remainder of the treatment and the return path voltage is then continuously measured. If the measured return path voltage is different form the target return path voltage indicative of target output current then the PWM value (duty cycle) is increased or decreased for the pulses delivered to the user. This is repeated until the required target output current is reached (the measured return path voltage equals the target return path voltage value). During use of the device this is preferably monitored and determined at every pulse. As the user moves contact with the pelvic floor will be improved or reduced resulting in the current delivered increasing or reducing. The device will adjust the PWM value to correct the output voltage of the device in order to maintain a constant target output current to the user. The placement of the device, hormonal cycle and tone of muscle from user to user will also affect the output voltage required to deliver the target output current. The microprocessor (100) has a PWM (duty cycle) which has a range of values typically required to achieve the required output voltage to effectively treat a range of users.

With reference to FIGS. 3 and 3(*a*), when it is desired to invoke a battery depletion routine this may be achieved under control of the microprocessor (100) by ensuring that output transistors OUTCONTROL1 and 2 are switched ON, whilst isolating the electrodes and continuing to draw power from the battery to provide a continuing BOOST cycle until the battery is depleted as power is drained through the inductor. Typically the device will cycle at 10V boost level until the battery is depleted and fully discharged.

Figure 4:
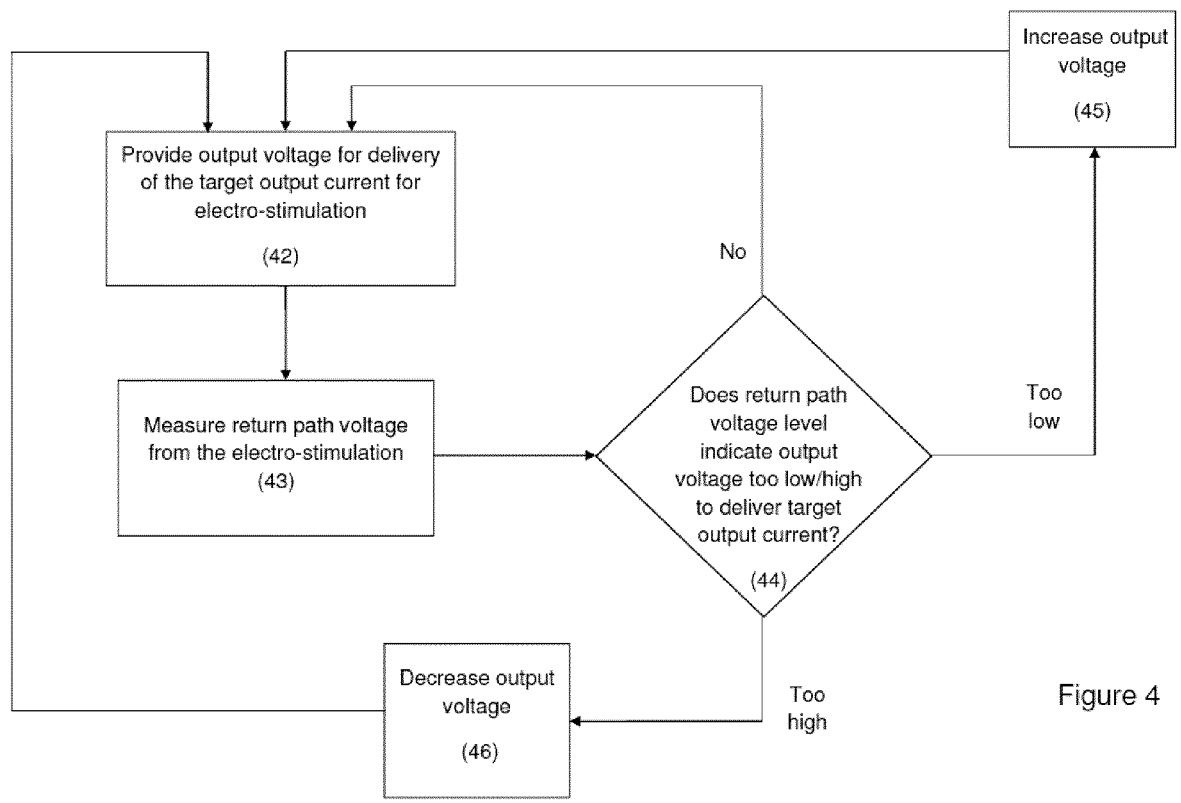
FIG. 4 shows a set of steps of a method according to an embodiment of the invention.

FIG. 4 is a diagram illustrating the general method of the present invention at step (42) the device under microprocessor control provides the appropriate output voltage for delivery of the desired target output current for electrostimulation and this is delivered to the muscle as a pulse of electro-stimulation. Then at step (43) the muscle has contracted under electro-stimulation and the return path voltage is measured. As indicated this is preferably measured at 30 μs after the muscle has started to contract. At step (44) the microprocessor uses the measured return path voltage at step (43) to determine if the output voltage delivered at step (42) was too high or too low to deliver the target output current. If it is determined that the output voltage at step (42) was neither too high or too low and actually delivered the target output current to the muscle then step (42) is simply repeated; if this is consistently the result at step (44) then the cycle of steps 42 to 44 and return to 42 is simply repeated until a variance is determined at step (44). If a variance is determined at step (44), which indicates that the output voltage at step (42) was too low to achieve the target output current then a further step (45) is invoked to increase the output voltage delivered at step (42). If a variance is determined at step (44), which indicates that the output voltage at step (42) was too high to achieve the target output current then a further step (46) is invoked to increase the output voltage delivered at step (42). Thus by determining the return path voltage at step (43) and using that value at step (44) in a determination of the accuracy of the output voltage at step (42) for delivery of the target output current the device is able to consistently deliver target output current to a user. This routine illustrated in FIG. 4 is ideally undertaken at each and every pulse in the treatment cycle.

Figure 5:
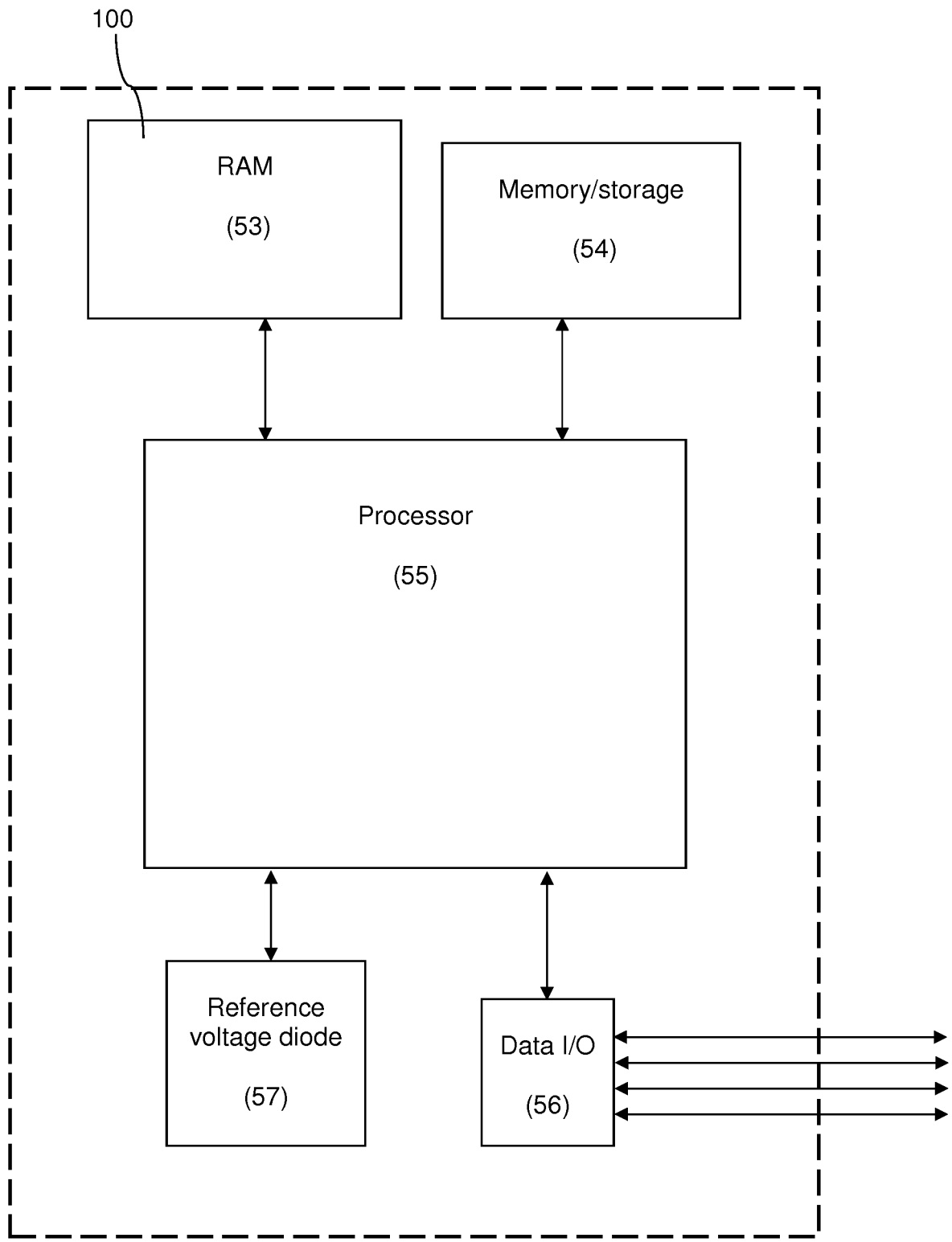
FIG. 5 shows components of a microprocessor according to an embodiment of the invention.

FIG. 5 is a diagram illustrating the microprocessor (100) from the previous Figures. It should be noted that certain of the above embodiments of the invention may be conveniently realized as a computer-implemented or processor-implemented system suitably programmed with instructions for carrying out the steps of the methods according to embodiments of the invention. The computing device or system may include software and/or hardware for providing functionality and features described herein. For example, FIG. 1 illustrates a housing which contains components of the device, FIGS. 3 and 3a illustrate components of the hardware inside the housing which implement features of the invention, and the microprocessor 100 which may be programmable with such instructions. In alternative embodiments, the programmable elements contained by the housing may take different forms, and indeed some features of the invention may be implemented by external computer-implemented or processor/controller systems which are adapted to communicate with the device 1 via electrodes 8 before and after use of the device.

The computing device(s) or system(s) may include one or more of logic arrays, memories, analogue circuits, digital circuits, software, firmware and processors. The hardware and firmware components of the device/system may include various specialized units, circuits, software and interfaces for providing the functionality and features described herein. For example, a central processing unit such as the microprocessor 100 is able to implement such steps as instructing provision of an initial output voltage for delivery of the target output current for electro-stimulation, and measuring a return path voltage at a specified period of the return voltage pulse.

The microprocessor (100) shown in FIG. 5 may be or include one or more microprocessors or processors such as processor 55 shown in FIG. 5, and in other embodiments, the processing used in the device may include application specific integrated circuits (ASICs), programmable logic devices (PLDs) and programmable logic arrays (PLAs).

Data can be received and transmitted by ports or interfaces or data I/O (56), for example providing the inputs and outputs described above regarding microprocessor 100 (U1 in FIG. 3/3a). The data I/O can also provide communication with external components, which may provide instruction or further processing. Such components could provide a direct link with apparatus or a connection to a network. For example, in embodiments of the invention the external connection may be to a networked user device, with which a user interacts.

In embodiments, software applications loaded on memory 54 may be executed to process data in random access memory 53. The memories 53 and/or 54 may be or include RAM, ROM, DRAM, SRAM and MRAM, and may include firmware, such as static data or fixed instructions, BIOS, system functions, configuration data, and other routines used during the operation of the computing device and/or processor. For example, the RAM 53 may store data such as reference or standard values of return voltage, or previous values of voltage output, and the memory 54 may store the software instructions to implement methods such as determining the next output voltage value based on the latest return voltage.

The memory also provides a storage area for data and instructions associated with applications and data handled by the processor. The storage provides non-volatile, bulk or long term storage of data or instructions in the computing device or system. Multiple storage devices may be provided or available to the microprocessor 100 or any external computing device/system, for the latter of which some may be external, such as network storage or cloud-based storage.

The computer or processor implementable instructions or software may for example contain separate modules or components for handling certain of the following steps of methods according to embodiments of the invention: generating a required output voltage level to achieve a target output current; measuring return path voltage through the muscle; adjusting the output voltage required to achieve the target output current for subsequent electro-stimulation based on the measurement of return path voltage; or determining a return voltage over a portion of the return voltage pulse, or at a specific point of the pulse.

In embodiments, the microprocessor 100 also houses, as described above, the voltage reference diode (57), which allows for example the memories 53 and 54 storing values and instructions to the processor (55) to scale the voltage value returned according to the true level of the battery.

All of the features disclosed in this specification for each and every aspect and/or embodiment (including any accompanying claims, abstract and drawings), and/or all of the steps of any method or process so disclosed, may be combined in any combination, except combinations where at least some of such features and/or steps are mutually exclusive.

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise. Features, integers, characteristics, compounds described in conjunction with a particular aspect, embodiment or example of the invention are to be understood to be applicable to any other aspect, embodiment or example described herein unless incompatible therewith.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. An electro stimulation device for delivering a target pulsed output current to muscle in contact with the device, which device comprises:
   a) a device body capable of being completely insertable into and removable from a vagina or anus,
   b) at least two electrodes for delivery of pulsed electro-stimulation current to muscle, c) at least one source of power,
   d) at least one control unit configured to:
     generate a required output voltage to achieve a target output current,
     measure return path voltage through the muscle from an initial decay period of an electro-stimulation pulse of a duration in the range of 100 to 350 μs at a single point between 20 to 40 μs after the start of the electro-stimulation pulse, and adjust the output voltage required to achieve a target output current for subsequent electro-stimulation based on the point measurement of the return path voltage.

2. A device according to claim 1, wherein the device is a self-contained device.

3. A device according to claim 1, further comprising a resistor for measuring the return path voltage through the muscle.

4. A device according to claim 3, wherein the resistor for measuring return path voltage has a resistance of from 10 to 100 ohms.

5. A device according to claim 1, wherein the power source is a battery.

6. A device as claimed in claim 1, further comprising a PCB with a microprocessor control unit internally within the device.

7. A device as claimed in claim 1 wherein the device further comprises isolation of the battery power source from the PCB and wherein the isolation is removable prior to use of the device.

8. A device as claimed in claim 7 wherein the isolation is a removable tab exposed to the exterior of the device and located internally between the internal battery and the internal PCB.

9. A device according to claim 1 further comprising a voltage limit.

10. A device according to claim 9 wherein the voltage limit comprises a Zener diode.

11. A device as claimed in claim 1 wherein the control unit is further configured for adjusting the output voltage of the device and/or any other voltage readings relative to the battery power level.

12. A device as claimed in claim 1 further comprising a reference voltage for battery power level determination.

13. A device as claimed in claim 12 wherein the reference voltage is provided via a fixed voltage reference point within the control unit circuit.

14. A device as claimed in claim 13 wherein the fixed voltage reference point is a diode of fixed voltage.

15. A device as claimed in claim 1, wherein the device is for delivering a target output current to the muscles of the pelvic floor either for treatment or exercise of the pelvic floor.

16. A device as claimed in claim 1 which further comprises data storage for storing the operating conditions, measured values and determined values used or determined during operation of the device.

17. A device as claimed in claim 16, which is adapted for access to the storage to read stored data during operation of the device.

18. A device as claimed in claim 16, which is adapted for access to the storage to read stored data after operation of the device is terminated or completed.

19. A device as claimed in claim 18, wherein the adaptation enables connection of the device via its electro conductive elements to a computer in order to read and/or copy data stored in the device to a computer for processing and/or storage on the computer.

20. A device as claimed in claim 1 further configured to generate an initial constant voltage phase during electro-stimulation.

21. A device as claimed in claim 1 further configured to generate a current ramp mode during electro-stimulation.

22. A device as claimed in claim 1 further configured to detect contact of the device with pelvic floor muscle.

23. A device as claimed in claim 1 wherein the at least one control unit is programmed to discharge any residual internal battery power on completion or interruption of the electrostimulation treatment cycle.

24. A device as claimed in claim 22, wherein the at least one control unit is configured to detect contact of the device with the pelvic floor muscle and to measure return path voltage through the muscle.

25. A method of delivering a target pulsed output current for electro-stimulation of a muscle, comprising: providing an initial output voltage for delivery of the target output current for electro-stimulation; measuring a return path voltage from the electro-stimulated muscle; and where a return path voltage level indicates that the initial output voltage differs from that required for delivery of the target pulsed output current, adjusting the output voltage, wherein the step of measuring the return path voltage comprises measuring a voltage level from an initial decay period of a returned electro-stimulation pulse of a duration within the range of 100 to 350 μs at a single point between 20 to 40 μs after the start of the electro-stimulation pulse.

26. A method according to claim 25, comprising comparing the return path voltage to a target return path voltage related to the output voltage required for delivery of the target output current.

27. A method according to claim 26, wherein a target value for the target return path voltage is a root mean square voltage.

28. A method according to claim 26, wherein the target output current is a root mean square current.

29. A method according to claim 25, wherein the specified period is between 25 to 35 μs after the start of the returned electro-stimulation pulse.

30. A method according to claim 25, wherein the specified period is between 27.5 to 32.5 μs after the start of the returned electro-stimulation pulse.

31. A method according to claim 25, wherein the specified period is 30 μs after the start of the returned electro-stimulation pulse.

32. A method according to claim 25, wherein the return path voltage is determined as a root mean square voltage of the pulse.

33. A method according to claim 25, wherein the step of adjusting the output voltage comprises sequentially adjusting the voltage for successive measurements of return path voltage, wherein the sequence of adjustments falls within a given range of voltages.

34. A method according to claim 25, wherein the step of adjusting the output voltage comprises using pulse width modulation to vary the output voltage.

35. A media device storing computer program code adapted, when loaded into or run on a computer or processor, to cause the computer or processor to carry out a method according to claim 25.

* * * * *